(12) United States Patent
Exner et al.

(10) Patent No.: US 9,132,149 B2
(45) Date of Patent: Sep. 15, 2015

(54) TOXICITY ENHANCING COMPOUNDS AND METHODS

(75) Inventors: Agata Exner, Westlake, OH (US); Bryan J. Traughber, Shaker Heights, OH (US); Tianyi Krupka, Westlake, OH (US); Reshani Perera, Mayfield Village, OH (US); David Dremann, Champaign, IL (US)

(73) Assignee: Case Western Reserve University, Cleveland, OH (US)

( * ) Notice: Subject to any disclaimer, the term of this patent is extended or adjusted under 35 U.S.C. 154(b) by 247 days.

(21) Appl. No.: 13/415,538

(22) Filed: Mar. 8, 2012

(65) Prior Publication Data
US 2012/0225027 A1    Sep. 6, 2012

Related U.S. Application Data

(63) Continuation-in-part of application No. 11/947,375, filed on Nov. 29, 2007.

(60) Provisional application No. 61/450,430, filed on Mar. 8, 2011.

(51) Int. Cl.
*A61K 31/765* (2006.01)
*A61K 41/00* (2006.01)

(52) U.S. Cl.
CPC ........... *A61K 31/765* (2013.01); *A61K 41/0038* (2013.01)

(58) Field of Classification Search
CPC .......................... A61K 41/0038; A61K 31/765
See application file for complete search history.

(56) References Cited

U.S. PATENT DOCUMENTS

| | | | | |
|---|---|---|---|---|
| 5,595,756 A | * | 1/1997 | Bally et al. | 424/450 |
| 2008/0206187 A1 | * | 8/2008 | Exner et al. | 424/78.31 |

OTHER PUBLICATIONS

Auerbach et al. Cancer and Metastasis Reviews, 2000, 19: 167-172.*
Sporn et al. "Chemoprevention of Cancer," Carcinogenesis, vol. 21 (2000), 525-530.*
Sigma Aldrich—"Surfactants Classified by HLB Numbers." Retrieved on Oct. 17, 2013. Retrieved from the internet <URL: http://www.sigmaaldrich.com/materials-science/material-science-products.printerview.html?TablePage=22686648>.*
Kabanov et al (2002). "Pluronic Block Copolymers in Drug Delivery: from Micellar Nanocontainers to biological Response modifiers." Critical Reviews in Therapeutic Drug Carrier Systems, 19(1): 1-73.*
Belenkov et al (2004) "Polyethyleneimine grafted with pluronic P85 enhances Ku86 antisense delivery and the ionization treatment efficacy in vivo." Gene Therapy, 11: 1665-1672.*
Venne et al (1996). "Hypersensitivity Effect of Pluronic L61 on Cytoxicity Activity, Transport, and Subcellular Distribution of Doxorubicin in Multiple Drug-Resistance Cells." Cancer Therapy, 56: 3626-3629.*
Batrakova et al (1999). "Fundamental Relationship Between the Composition of Pluronic Block Copolymers and Their Hypersensitization Effect in MDR Cancer Cells." Pharmaceutical Research, 16(9): 1373-1379.*

* cited by examiner

*Primary Examiner* — Anoop Singh
*Assistant Examiner* — Doan Phan
(74) *Attorney, Agent, or Firm* — Tarolli, Sundheim, Covell & Tummino LLP

(57) ABSTRACT

A method of treating a tumor or cancer in a subject includes administering to cancer or tumor cells of the subject a radiation sensitizing amount of a poly(ethylene oxide)-poly(propylene oxide) copolymer and administering radiation therapy to the cancer or tumor cells sensitized by the poly(ethylene oxide)-poly(propylene oxide) copolymer.

22 Claims, 14 Drawing Sheets

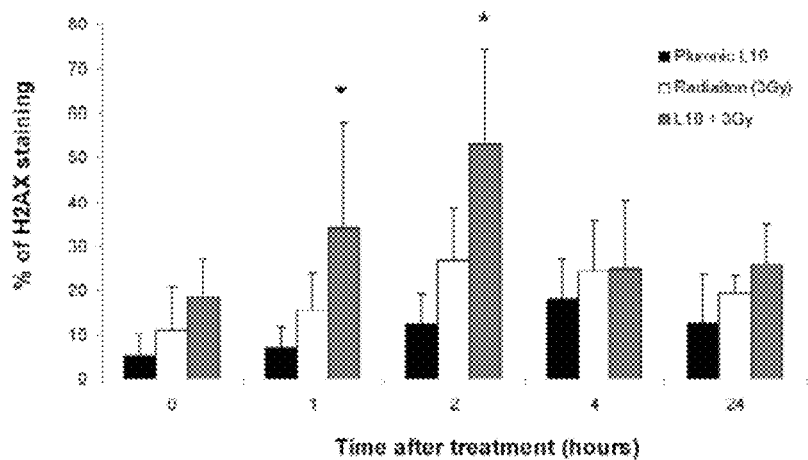
Fig. 16
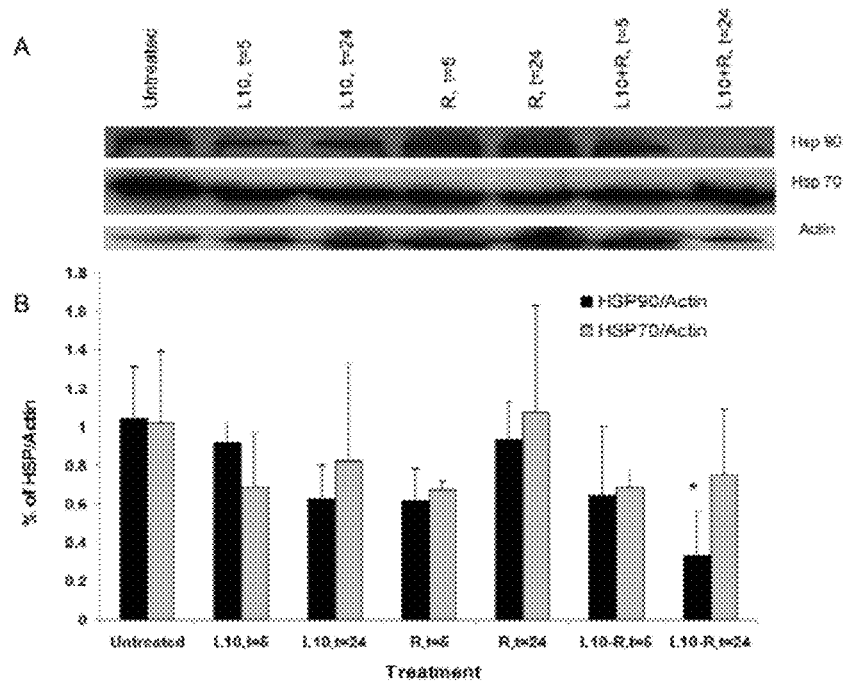
Figs. 17A-B

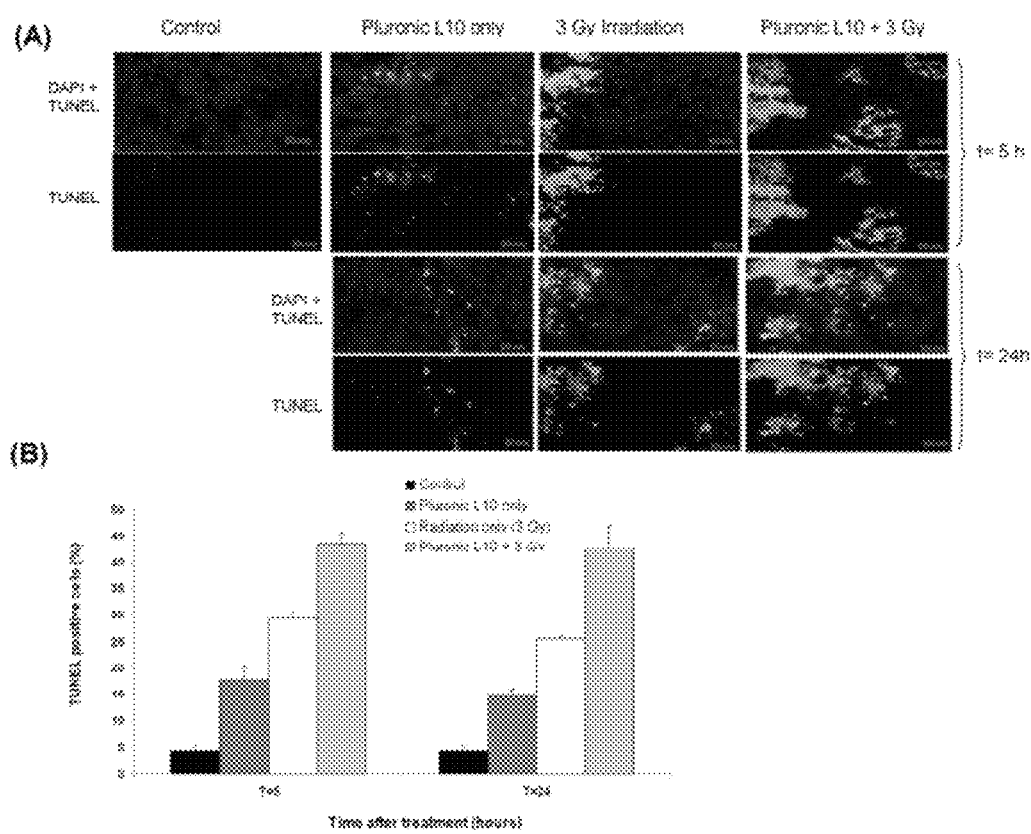
Figs. 18A-B

TOXICITY ENHANCING COMPOUNDS AND METHODS

RELATED APPLICATION

This application claims priority from U.S. Provisional Application No. 61/450,430, filed Mar. 8, 2011, and is a Continuation-in-Part of U.S. application Ser. No. 11/947,375, filed Nov. 29, 2007, the subject matter of which are incorporated herein by reference in their entirety.

GOVERNMENT FUNDING

This invention was made with government support under Grant Nos. CA136857 and CA118399, awarded by The National Institutes of Health. The United States government may have certain rights to the invention.

TECHNICAL FIELD

This application generally relates to compositions and methods for sensitizing neoplastic cells and microorganisms to stress, and more particularly relates to polymers that can be used to sensitize neoplastic cells and microorganisms to stress.

BACKGROUND

Radiation therapy is one of the widespread and effective treatment modalities for cancer patients. Despite demonstrated advantages, there are some drawbacks of radiotherapy including, normal tissue damage, and radiation tolerance of tumors. The outcome of the radiation treatment is primarily determined by the radiosensitivity of tumor cells. Much attention has been focused on studying the molecular machinery behind radiation tolerance or radioresistance of tumors. A commonly studied target is heat shock proteins.

Heat shock proteins (Hsp) are well described molecular chaperones that are intricately involved in the folding, stability, activation and maturation of key proteins involved in the cell cycle and signal transduction. Hsp90 and 70 are perhaps the best studied chaperones in the heat shock family that have been linked to cancer.

Hsp70 is responsible for helping in the natural cycle of protein folding post ribosomal production, assisting improperly folded proteins (either naturally or from external stresses such as hyperthermia) to either realize their optimal tertiary folded conformation, to facilitate protein sequestration, and to regulate protein degradation. This protein maintenance function is highly important because if damaged proteins are not either selectively refolded to regain functioning or degraded they will begin to accumulate in the cytosol effectively interfering with established signaling pathways thereby clogging the cellular mechanisms inducing apoptosis.

The expression of Hsp90 is known to be up-regulated in malignant type compared to the normal tissues. Many Hsp90 client proteins are known to be involved in cancer metastasis, invasion, and angiogenesis. Hsp90 stabilizes proteins such as, Raf-1, Akt and ErbB2 that promote cellular survival by protecting from radiation induced cell death. Inhibition of Hsp90 causes inactivation of these client proteins increasing tumor cell death in numerous cell lines and tumor models. A variety of Hsp90 inhibitors have been reported and demonstrated the inhibitory effects of enhancing radiosensitivity in various histologies. However, research has shown that inhibition of Hsp90 typically causes up-regulation of Hsp70, ultimately limiting the outcome of Hsp90 inhibition for cancer cell death.

SUMMARY

An aspect of this application relates to a method of treating a tumor or cancer in a subject. The method includes administering to cancer or tumor cells of the subject a radiation sensitizing amount of a poly(ethylene oxide)-poly(propylene oxide) copolymer and administering radiation therapy to the cancer or tumor cells sensitized by the poly(ethylene oxide)-poly(propylene oxide) copolymer. The tumor or cancer can be radiation resistant and the administered poly(ethylene oxide)-poly(propylene oxide) copolymer can sensitize the tumor or cancer cells to radiation therapy. The poly(ethylene oxide)-poly(propylene oxide) copolymer can administered at an amount effective to reduce Hsp expression and/or function in the cancer cell or tumor cell induced by either external beam or internal source radiation therapy.

In some aspects, the copolymer can be selected from the group consisting of poloxamers, poloxamines, and combinations thereof. The poloxamer can include the chemical formula of HO—$(C_2H_4O)_a(C_3H_6O)_b(C_2H_4O)_a$—H, where "a" is about 2 to about 130 and "b" is about 16 to about 67. The poloxamer can also have a molecular weight of about 1100 Da to about 3200 Da, a hydrophilic lipophilic balance (HLB) of about 1 to about 8, and dose enhancement factor (DEF) of at least 1.3.

In other aspects, the poly(ethylene oxide)-poly(propylene oxide) copolymer can be administered directly to the tumor or cancer cells or systemically to the subject. The systemic administration can be by parenteral administration or by intravenous injection.

BRIEF DESCRIPTION OF THE DRAWINGS

FIG. 16 illustrates a table showing percentage of cells with γ-H2AX staining after irradiation (3 Gy) with and without pretreatment with 0.3 mg/ml Pluronic L10.

FIG. 17 illustrates: (A) Western blots of Hsp90 and Hsp70 protein analysis from Gli36 tumor xenografts after 1 hr pretreatment of Pluronic L10 (0.3 mg/ml), radiation only (3 Gy), and combined treatment; and (B) a table showing Hsp expression at different time points normalized versus actin.

FIG. 18 illustrates: (A) images showing TUNEL staining of Gli36 xenografted tumor sections after irradiated with 3 Gy with and without 1 hr pretreatment with Pluronic L10 (0.3 mg/ml): and (B) a table showing TUNEL positive cells expressed as the percentage of total cell number.

DETAILED DESCRIPTION

Figure 1:
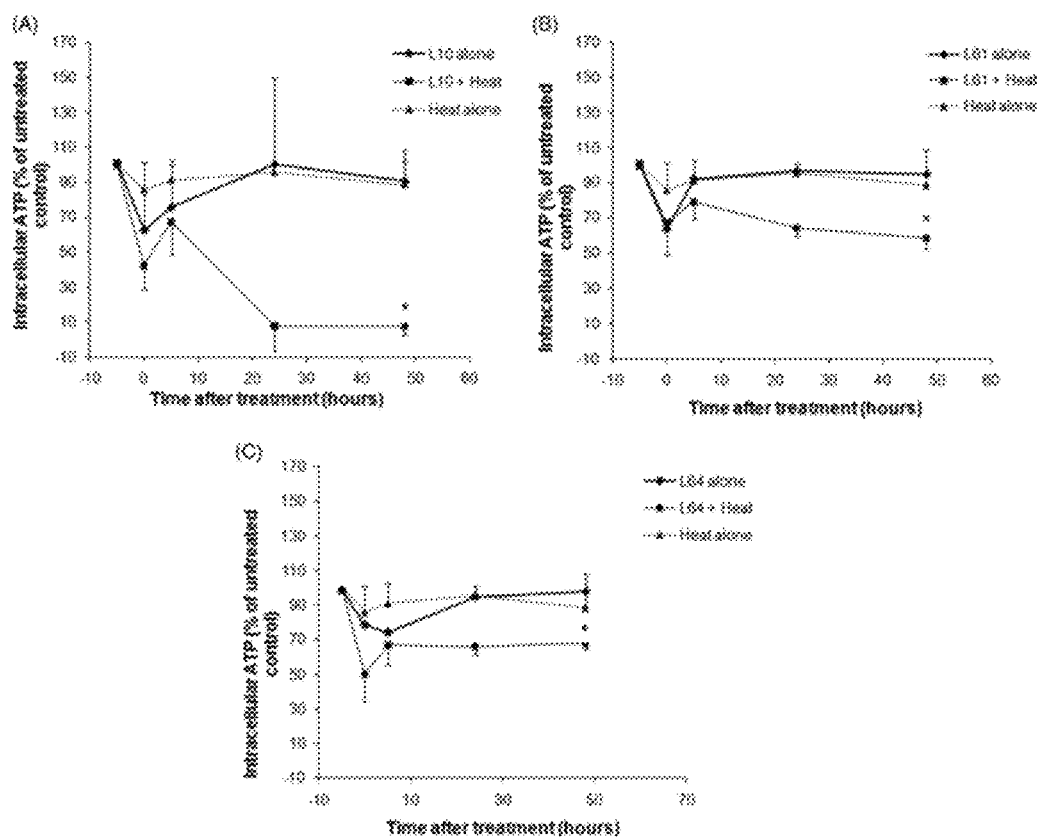
FIG. 1 illustrates plots showing intracellular ATP levels in DHD/K12/TRb cells treated with heat only (43°±0.05° C. for 20 min), Pluronic L10 (A), L61 (B), L64 (C) alone and combined (Pluronic+heat) treatment. *Indicates statistically significant difference (P<0.05) compared to the untreated control (n=3±STDEV).

All scientific and technical terms used in this application have meanings commonly used in the art unless otherwise specified. The definitions provided herein are to facilitate understanding of certain terms used frequently herein and are not meant to limit the scope of the application.

As used herein, the term "subject" refers to any mammal including but not limited to human, non-human primate, cow, horse, pig, sheep, goat, dog, cat or rodent.

As used herein, the term "neoplastic disorder" refers to a disease state in a subject in which there are cells and/or tissues which proliferate abnormally. Neoplastic disorders can include, but are not limited to, cancers, sarcomas, tumors, leukemias, lymphomas, and the like.

As used herein, the term "neoplastic cell" refers to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. Alternatively, a neoplastic cell can be termed a "cancer cell." Non-limiting examples of cancer cells can include lymphoma cells, melanoma cells, sarcoma cells, leukemia cells, retinoblastoma cells, hepatoma cells, myeloma cells, glioma cells, mesothelioma cells, carcinoma cells and adenocarcinoma cells.

As used herein, the term "tumor" refers to an abnormal mass or population of cells that result from excessive cell division, whether malignant or benign, and all pre-cancerous and cancerous cells and tissues.

As used herein, the terms "treating" or "treatment" refer to executing a treatment protocol, which may include administering a cell-sensitizing composition into a subject and then applying stress to eradicate at least one cancer cell, tumor cell, or microorganism. Thus, "treating" or "treatment" does not require complete eradication of cancer and tumor cells or microorganisms.

As used herein, the term "effective amount" refers to an amount of a composition that is sufficient to fulfill its intended purpose(s). In the context of the application, the purpose(s) may be, for example: to inhibit or reduce the expression of at least one heat shock protein in cancer or tumor cells; and/or to promote hyperthermia of a sensitized cancer cells, tumor cells or microorganisms; and/or to potentiate the biocidal or biostatic properties of an antimicrobial agent; and/or to delay or prevent the onset of a microbial infection.

As used herein, the term "polymer" refers to a molecule formed by the chemical union of two or more chemical units. The chemical units may be linked together by covalent linkages. The two or more combining units in a polymer can be all the same, in which case the polymer may be referred to as a homopolymer. The chemical units can also be different and, thus, a polymer may be a combination of the different units. Such polymers may be referred to as copolymers.

As used herein, the term "block copolymer" refers to a polymer in which adjacent polymer segments or blocks are different, i.e., each block comprises a unit derived from a different characteristic species of monomer or has a different composition of units.

As used herein, the term "poloxamer" refers to a series of non-ionic surfactants comprised of block copolymers of ethylene oxide and propylene oxide. Poloxamers are synthesized by the sequential addition of propylene oxide, followed by ethylene oxide, to propylene glycol. The poly(oxyethylene) segment is hydrophilic and the poly(oxypropylene) segment is hydrophobic. The molecular weight of poloxamers may range from 1000 to greater than 16000. The basic structure of a poloxamer is $HO-(C_2H_4O)_a(C_3H_6O)_b(C_2H_4O)_a-H$, where "a" and "b" represent repeating units of ethylene oxide and propylene oxide, respectively.

As used herein, the term "poloxamine" refers to a polyalkoxylated symmetrical block copolymer prepared from an ethylene diamine initiator. Poloxamines are synthesized using the same sequential order of addition of alkylene oxides as used to synthesize poloxamers. Structurally, the poloxamines include four alkylene oxide chains and two tertiary nitrogen atoms, at least one of which is capable of forming a quaternary salt. Poloxamines are also terminated by primary hydroxyl groups.

As used herein, the terms "radiation therapy" or "radiotherapy" refer to the use of high-energy radiation from x-rays, gamma rays, neutrons, protons, and other sources to kill cancer cells and shrink tumors. Radiation may come from a machine outside the body (external-beam radiation therapy), or it may come from radioactive material placed in the body near cancer cells (internal radiation therapy). Systemic radiation therapy uses a radioactive substance, such as a radiolabeled monoclonal antibody, that travels in the blood to tissues throughout the body. The terms are intended to include without limitation ionizing radiation therapy, brachytherapy, sealed source radiation therapy, systemic radioisotope therapy, unsealed source radiotherapy, radionuclide therapy, external beam radiation therapy, radiation surgery, charged-particle radiotherapy, neutron radiotherapy, x-ray therapy, gamma-ray therapy, and cobalt therapy.

As used herein, the term "ionizing radiation" means radiation comprising particles or photons that have sufficient energy or can produce sufficient energy via nuclear interactions to produce ionization (gain or loss of electrons). An exemplary ionizing radiation is an x-radiation or gamma-radiation.

As used herein, the term "cell-sensitizing composition" refers to a composition comprising at least one copolymer capable of increasing sensitivity or reducing resistance to stress. In some aspects, a "cell-sensitizing composition" refers to a composition comprising at least one copolymer capable of inhibiting Hsp expression in a cell exposed to or subjected to stress. By "sensitizing" it is meant that the cell exhibits an increased sensitivity or reduced resistance to stress. For example, increased sensitivity or reduced resistance of a tumor cell may be measured according to methods known in the art, e.g., cell proliferative assays, tumor volume reduction or a reduction in the rate of tumor volume increase.

As used herein, the "radiation sensitizing" or "radiation sensitizer" refers to compounds or methods of increasing a neoplastic cell susceptibility to ionizing radiation compared to normal cells and/or making neoplastic cells more susceptible to death than surrounding normal cells.

Embodiments of the application described herein relate to compositions and methods for treating neoplastic disorders (e.g., cancer or tumors) and microbial infections and potentiating the biocidal or biostatic properties of antimicrobial agents. It was found that poly(ethylene oxide)-poly(propylene oxide) copolymers can substantially decrease intracellular adenosine-5'-triphosphate (ATP) and Hsp expression or function (e.g., Hsp70 or Hsp90) in neoplastic cells or microorganisms subjected to stress sufficient to induce expression of heat shock proteins (Hsp). It is believed that exposure to or application of stress and ATP depletion can also concomitantly cause intracellular Hsp to remain bound to denaturing proteins rendering the indefinitely-bound Hsp an intracellular obstruction thereby leading to cell apoptosis and death. A cell-sensitizing composition described herein that includes a poly(ethylene oxide)-poly(propylene oxide) copolymer can therefore be administered to a neoplastic cell (e.g., tumor cell or cancer cell) or microorganism in combination with a stress sufficient to induce expression of heat shock proteins (Hsp) to inhibit growth and/or induce or promote apoptosis, necrosis, and/or death of the neoplastic cell or microorganism.

In some embodiments, the cell-sensitizing composition can be administered to the neoplastic cell and/or microorganism to reduce or inhibit Hsp expression. The Hsp expression inhibited can be Hsp70 and/or Hsp90 expression. In an exemplary embodiment, poly(ethylene oxide)-poly(propylene oxide) copolymers can inhibit Hsp70 and/or Hsp90 protein function as well as decrease the level of intracellular ATP in neoplastic cells thereby sensitizing neoplastic cells, such as tumor or cancer cells, exposed to stress.

In other embodiments, the cell-sensitizing composition may be responsive to, or affected by, stress. For example, the cell-sensitizing composition may undergo a phase shift when the temperature of the cell-sensitizing composition passes through a lower critical solution temperature (LCST). Above the LCST, the cell-sensitizing composition may tend to become dehydrated, in turn making it less soluble in water.

In some embodiments, the poly(ethylene oxide)-poly(propylene oxide) copolymer of the cell-sensitizing composition can include a block copolymer, such as a poly(ethylene oxide)-poly(propylene oxide) block copolymer. Examples of poly(ethylene oxide)-poly(propylene oxide) block copolymers are poloxamers, poloxamines, and combinations thereof.

The poloxamer can include any one or combination of a series of non-ionic surfactants including block copolymers of ethylene oxide and propylene oxide. The poly(oxyethylene) (PEO) and poly(oxypropylene) (PPO) segments are hydrophilic and hydrophobic, respectively. The poloxamer may be a liquid, a paste or a solid, and may have a molecular weight that ranges from about 1000 Da to greater than about 16000 Da.

The chemical formula of the poloxamer described herein is $HO-(C_2H_4O)_a(C_3H_6O)_b(C_2H_4O)_a-H$, where "a" and "b" represent repeating units of PEO and PPO, respectively. More particularly, the at least one poloxamer may have the chemical formula of $HO(C_2H_4O)_a(C_3H_6O)_b(C_2H_4O)_a-H$, where "a" is about 2 to about 130 and "b" is about 16 to about 67. It should be appreciated that the poloxamer may comprise a reverse poloxamer if the ethylene oxide segment is sandwiched between two propylene oxide segments (i.e., PPO-PEO-PPO).

Poloxamers are commercially available under various trade names including, for example, LUTROL, PLURONIC, SYNPERONIC (ICI), EMKALYX, PLURACARE, and PLURODAC. Examples of the PLURONIC series are PLURONIC L10 (MW: 3200 Da), PLURONIC L121 (MW: 4400 Da), PLURONIC L101 (MW: 3800 Da), PLURONIC L81 (MW: 2750 Da), PLURONIC L61 (MW: 2000 Da), PLURONIC L31 (MW: 1100 Da), PLURONIC L122 (MW: 5000 Da), PLURONIC L92 (MW: 3650 Da), PLURONIC L72 (MW: 2750 Da), PLURONIC L62 (MW: 2500 Da), PLURONIC L42 (MW: 1630 Da), PLURONIC L63 (MW: 2650 Da), PLURONIC L43 (MW: 1850 Da), PLURONIC L64 (MW: 2900 Da), PLURONIC L44 (MW: 2200 Da), PLURONIC L35 (MW: 1900 Da), PLURONIC P123 (MW: 5750 Da), PLURONIC P103 (MW: 4950 Da), PLURONIC P104 (MW: 5900 Da), PLURONIC P84 (MW: 4200 Da), PLURONIC P105 (MW: 6500 Da), PLURONIC P85 (MW: 4600 Da), PLURONIC P75 (MW: 4150 Da), PLURONIC P65 (MW: 3400 Da), PLURONIC F127 (MW: 12600 Da), PLURONIC F98 (MW: 13000 Da), PLURONIC F87 (MW: 7700 Da), PLURONIC F77 (MW: 6600 Da), PLURONIC F108 (MW: 14600 Da), PLURONIC F98 (MW: 13000 Da), PLURONIC F88 (MW: 11400 Da), PLURONIC F68 (MW: 8400 Da), and PLURONIC F38 (MW: 4700 Da).

Examples of reverse poloxamers are PLURONIC R 31R1 (MW: 3250 Da), PLURONIC R 25R1 (MW: 2700 Da), PLURONIC R 17R1 (MW: 1900 Da), PLURONIC R 31R2 (MW: 3300 Da), PLURONIC R 25R2 (MW: 3100 Da), PLURONIC R 17R2 (MW: 2150 Da), PLURONIC R 12R3 (MW: 1800 Da), PLURONIC R 17R4 (MW: 4150 Da), PLURONIC R 25R4 (MW: 1600 Da), PLURONIC R 22R4 (MW: 3350 Da), PLURONIC R 17R4 (MW: 3650 Da), PLURONIC R 25R5 (MW: 4320 Da), PLURONIC R 10R5 (MW: 1950 Da), PLURONIC R 25R8 (MW: 8550 Da), PLURONIC R 17R8 (MW: 7000 Da), and PLURONIC R 10R8 (MW: 4550 Da).

Other commercially available poloxamers can include compounds that are block copolymers of polyethylene and polypropylene glycol, such as SYNPERONIC L121, SYNPERONIC L122, SYNPERONIC P104, SYNPERONIC P105, SYNPERONIC P123, SYNPERONIC P85, SYNPERONIC P94, and compounds that are nonylphenyl polyethylene glycol such as SYNPERONIC NP10, SYNPERONIC NP30 and SYNPERONIC NP5.

In some embodiments, the poloxamer can have a molecular weight that ranges from about 1000 Da to about 4000 Da and a hydrophilic lipophilic balance (HLB) of about 1 to about 8. In other embodiments, the poloxamer can have a molecular weight of about 1100 Da to about 3200 Da and a HLB of about 1 to about 8. Poloxamers with a molecular weight of about 1100 Da to about 3200 Da and a HLB of about 1 to about 8 were shown in the Examples as being the most effective at sensitizing cancer or tumor cells to stress, such as radiation, without significant toxicity or very little effect on normal cells of the subject.

Examples of poloxamers with a molecular weight of about 1100 Da to about 3200 Da and a HLB of about 1 to about 8 are PLURONIC L10 (MW: 3200, HLB: 2), PLURONIC L64 (MW: 2900, HLB: 8), PLURONIC L62 (MW: 2500, HLB: 4), PLURONIC L61 (MW: 2000, HLB: 2), PLURONIC L31 (MW: 1100, HLB: 3.2), PLURONIC L44 (MW: 2200, HLB: 8) and PLURONIC L81 (MW: 2750, HLB: 2).

In other embodiments, the poly(ethylene oxide)-poly(propylene oxide) block copolymer can be a poloxamine. Poloxamines can include a polyalkoxylated symmetrical block copolymer prepared from an ethylene diamine initiator. Poloxamines are synthesized using the same sequential order of addition of alkylene oxides as used to synthesize poloxamers. Structurally, the poloxamines can include four alkylene oxide chains and two tertiary nitrogen atoms, at least one of which is capable of forming a quaternary salt. Poloxamines can also be terminated by primary hydroxyl groups. Examples of poloxamines are the TETRONIC and/or TETRONIC R series produced by BASF. For example, poloxamines can include TETRONIC 904, TETRONIC 908, TETRONIC 1107, TETRONIC 90R4, TETRONIC 1304, TETRONIC 1307 and TETRONIC T1501.

It will be appreciated that the cell-sensitizing composition may further comprise a pharmaceutically acceptable carrier. Pharmaceutically acceptable carriers may include any material or materials which are not biologically or otherwise undesirable, i.e., the material may be incorporated into the cell-sensitizing composition without causing any undesirable biological effects or interacting in a deleterious manner with any of the other components of the cell-sensitizing composition. When the term pharmaceutically acceptable is used to refer to a pharmaceutical carrier, it is implied that the carrier has met the required standards of toxicological and manufacturing testing or that it is included on the Inactive Ingredient Guide prepared by the U.S. Food and Drug administration.

The stress applied to the neoplastic cell or microorganism can include, for example, radiation therapy or ionizing radiation, thermal stress or thermal therapy, irreversible electroporation (IRE), oxidative stress, heavy-metals, infection, inflammation, anti-microbial agents, and combinations thereof.

Radiation therapy may include both "sealed" and "unsealed" sources of therapeutic radiation including, but not limited to, ionizing radiation therapy, brachytherapy, sealed source radiation therapy, systemic radioisotope therapy, unsealed source radiotherapy, radionuclide therapy, external beam radiation therapy, radiation surgery, charged-particle radiotherapy, neutron radiotherapy, x-ray therapy, gamma-ray therapy, and cobalt therapy.

Thermal stress or therapy can include focused ultrasound (FUS or HIFU), radiofrequency, infrared sauna, microwave heating, induction heating, magnetic hyperthermia, infusion of warmed liquids, or direct application of heat. The thermal stress can include local hyperthermia and/or regional hyperthermia. The thermal stress or thermal therapy can also include exposure to sub-lethal heat. For example, a hyperthermia modality may heat a cancer cell or microorganism too much lower therapeutic temperatures (in general <45° C.) compared to other tissue ablation techniques. For instance, the elevation above a normal body temperature of 37° C. typically will fall within a range of 42° C. to 45° C.

Irreversible electroporation uses a series of microsecond electrical pulses instead of extreme heat, freezing, radiation or microwave energy—to permanently open cell membranes in cancerous tumors. Once the cell membrane pores are opened, the death of the targeted cancer cells is induced. Surrounding veins, nerves and ducts within the targeted area are largely unaffected by the process around them, providing a compelling tool for procedures in difficult-to-treat parts of the body.

The exposure to stress may also be imaged guided. For example, clinical HIFU procedures are typically image-guided to permit treatment planning and targeting before applying a therapeutic or ablative level of ultrasound energy. When MRI is used for guidance, the technique is sometimes called Magnetic Resonance-guided Focused Ultrasound, often shortened to MRgFU. When ultrasonography is used, the technique is sometimes called Ultrasound-guided Focused Ultrasound, often shortened to USgFUS.

A neoplastic cell or microorganism can be pretreated with a cell-sensitizing composition prior to exposure to stress. For example, a cell-sensitizing composition may be administered to a neoplastic cell for an amount of time before the neoplastic cell is exposed to stress. Alternatively, a cell-sensitizing composition can be administered concomitantly with the exposure of the neoplastic cell or microorganism to stress.

In a particular embodiment, the cell-sensitizing composition comprising the poly(ethylene oxide)-poly(propylene oxide) copolymer can be used in combination with radiation therapy to inhibit tumor or cancer growth and/or promote apoptosis, necrosis, and/or tumor or cancer cell death. The tumor can include a solid tumor, such as a solid carcinoma, sarcoma or lymphoma, and/or an aggregate of neoplastic cells. The tumor may be malignant or benign, and can include both cancerous and pre-cancerous cells. In some embodiments, tumor or cancer can be radiation resistant. By radiation resistant it is meant that the cancer or tumor is resistant to treatment by radiation therapy. In some embodiments, the cancer or tumor can include gliomas, glioblastoma multiform (GBM), colorectal cancer, breast cancer, liver cancer, and/or melanoma.

A subject having cancer, tumor, or at least one cancer or tumor cell, may be identified using methods known in the art. For example, the anatomical position, gross size, and/or cellular composition of cancer cells or a tumor may be determined using contrast-enhanced MRI or CT. Additional methods for identifying cancer cells can include, but are not limited to, ultrasound, bone scan, surgical biopsy, and biological markers (e.g., serum protein levels and gene expression profiles). As described in greater detail below, an imaging solution comprising a cell-sensitizing composition of the present invention may be used in combination with MRI or CT, for example, to identify cancer cells.

A cell-sensitizing composition comprising the poly(ethylene oxide)-poly(propylene oxide) copolymer may be administered to the cancer or tumor cell at an amount effective to sensitize the cancer or tumor cells to radiation therapy. As noted above, the cell-sensitizing composition can include a poly(ethylene oxide)-poly(propylene oxide) block copolymer, such as a poloxamer. In some embodiments, the poloxamer can have a molecular weight of about 1100 Da to about 3200 Da and a HLB of about 1 to about 8. Examples of poloxamers with a molecular weight of about 1100 Da to about 3200 Da and a HLB of about 1 to about 8 are PLURONIC L10 (MW: 3200, HLB: 2), PLURONIC L64 (MW: 2900, HLB: 8), PLURONIC L62 (MW: 2500, HLB: 4), PLURONIC L61 (MW: 2000, HLB: 2), PLURONIC L31 (MW: 1100, HLB: 3.2), PLURONIC L44 (MW: 2200, HLB: 8) and PLURONIC L81 (MW: 2750, HLB: 2).

The location(s) where the cell-sensitizing composition is administered to the subject may be determined based on the subject's individual need, such as the location of the cancer cells (e.g., the position of a tumor, the size of a tumor, and the location of a tumor on or near a particular organ). For example, the cell-sensitizing composition may be injected directly (i.e., intratumorally) into a tumor. Alternatively, the cell-sensitizing composition may be injected intravenously into the subject. It will be appreciated that other routes of injection may be used including, for example, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal routes.

Before, after, or during sensitization of the cancer or tumor cells with the cell-sensitizing composition, radiation therapy or ionizing radiation can be applied to the sensitized cancer or tumor cells. As described above, radiation therapy may include ionizing radiation therapy, brachytherapy, sealed source radiation therapy, systemic radioisotope therapy, unsealed source radiotherapy, radionuclide therapy, external beam radiation therapy, radiation surgery, charged-particle radiotherapy, neutron radiotherapy, x-ray therapy, gamma-ray therapy, and cobalt therapy.

The radiation therapy can also be administered at a lower dose or sub-lethal dose and still achieve a therapeutic effect due to the radiation sensitizing effect of the poly(ethylene oxide)-poly(propylene oxide) copolymer.

In some embodiments, an additional sensitizing solution may be administered to the subject before, during, or after exposure cancer or tumor site to radiation. The sensitizing solution may comprise a sodium chloride solution, such as saline, and may be administered directly into the sensitized cancer or tumor cells or intravenously. Alternatively, the sensitizing solution may be combined with the cell-sensitizing composition and then injected into the subject.

The anatomical and physiological effects of radiation delivery to the sensitized cancer or tumor cells may be monitored using techniques known in the art. For example, functional MRI (fMRI), MR spectroscopy (MRS) or functional CT may be used to monitor longitudinal changes in tissue perfusion and/or metabolism within the sensitized cancer or tumor cells as radiation is being applied. Other techniques, such as cell viability and/or proliferation assays, may also be used to monitor the effects of energy delivery to the sensitized cancer or tumor cells. Depending upon the observed effects of radiation delivery to the sensitized cancer or tumor cells, the method may be repeated as needed. For example, if fMRI indicates that a tumor is partially ablated, then energy may be re-applied to the tumor until the tumor is entirely ablated.

In an example of a method described herein, a human subject having a solid tumor, such as a colorectal carcinoma, may be treated with the cell-sensitizing composition and radiation therapy. Prior to treatment, as described above, the location, size, and type of the carcinoma may be identified using contrast-enhanced MRI or CT. A cell-sensitizing composition including about 0.01 mg/ml to about 1.00 mg/ml of a Pluronic (e.g., PLURONIC L:10) can be administered to the carcinoma by, for example, intravenous infusion into the subject or direct injection into the carcinoma. After administering an amount of cell-sensitizing composition, radiation may be applied to the carcinoma according to FDA Regulatory Limits (See Title 21 CFR Part 361). In an exemplary embodiment, ionizing radiation can be applied to the carcinoma at about 100 to about 800 Rad. Advantageously, the carcinoma can be pretreated with the cell-sensitizing composition prior to administering the radiation therapy to reduce the radiation needed to achieve the same therapeutic effect. In an exemplary embodiment, a carcinoma may be pretreated with a cell-sensitizing composition for about 2 hours prior to radiation therapy.

The carcinoma may be imaged using CT or MRI, for example, during and/or after delivery of radiation to assess any longitudinal changes in carcinoma tissue perfusion and/or metabolism within the carcinoma. Administration of the cell-sensitizing composition and radiation therapy can be repeated as needed until the desired therapeutic effect is achieved, e.g., reduction in tumor size and/or cancer or tumor cell apoptosis or death.

Optionally, at least one chemotherapeutic agent may be administered to the subject in conjunction with or after applying radiation to the sensitized cancer or tumor cells. Examples of chemotherapeutic agents include, but are not limited to, doxorubicin, cisplatin, etoposide, vinblastine, vincristine, estrumustine, suramin, staurosporine, paclitaxel, angiogenstatin, and estastatin. Administering a chemotherapeutic agent helps to ensure that any non-ablated cancer or tumor cells are destroyed (e.g., complete tumor eradication).

Other embodiments of the application relate to compositions and methods sensitizing microorganisms, such as bacteria and fungus, resistant to antimicrobial agents that would otherwise be ineffective. It is contemplated that poly(ethylene oxide)-poly(propylene oxide) copolymer compositions may be integrated into routine cleaning and sterilization supplies utilized in the healthcare setting, such as disinfectants and antiseptics. Many hospital organisms, such as MRSA and Pseudomonas, are often resistant to standard agents and using a bioactive poly(ethylene oxide)-poly(propylene oxide) copolymer within these agents may render them more effective and decrease rates of nosocomial infection. For example, a poly(ethylene oxide)-poly(propylene oxide) copolymer composition may be added to a disinfectant or antiseptic at an amount effective to potentiate the biocidal or biostatic properties of antimicrobial agent.

Therefore, an aspect of the application relates to an antimicrobial composition that includes at least one biocidal agent or biostatic agent and an amount of a poly(ethylene oxide)-poly(propylene oxide) copolymer effective to potentiate the biocidal or biostatic properties of the biocidal or biostatic agent. Biocidal agents and biostatic agents that can be used in the methods and materials of this invention include agents that kill microbes as well as agents that simply inhibit their growth or accumulation. For health reasons, biocidal or biostatic agents that inhibit the growth of microorganisms are preferably used for materials that are to be used in, for example, consumer products.

Biocidal agents and biostatic agents can include anti-microbial agents, anti-fungals, antibiotics, anti-parasitics, disinfective agents, sanitizing agents, and chemisterillant (sterilant) agents such as those listed in United States Pharmacopeial Convention, Inc. United States Pharmacopeia 28-National Formulary 23. Rockville, Md.: US Pharmacopeial Convention, Inc.; 2004: 61-62, 227-228, 439-441, 943-944, 972, 1029, 1077, 1532-1533, 1601, 1786, 2964-2965.

Examples of biocidal agents and biostatic agents include: alcohol, glycol, aldehyde and acids; iodophors such as iodine or povidone iodine; oxidizing agents such as hydrogen peroxide or sodium hypochlorite; phenols and related compounds such as hexacholophene; surface-active agents such as chlorohexidine and quaternarium ammonium and derivatives.

Additional examples of biocidal agents and biostatic agents include, but are not limited to, phenolic and chlorinated phenolic compounds, resorcinol and its derivatives, bisphenolic compounds, benzoic esters (parabens), halogenated carbonilides, polymeric antimicrobial agents, thazolines, trichloromethylthioimides, natural antimicrobial agents (also referred to as "natural essential oils"), metal salts, and broad-spectrum antibiotics.

Specific phenolic and chlorinated phenolic biocidal agents and biostatic agents that can be used in the invention include, but are not limited to: phenol; 2-methyl phenol; 3-methyl phenol; 4-methyl phenol; 4-ethyl phenol; 2,4-dimethyl phenol; 2,5-dimethyl phenol; 3,4-dimethyl phenol; 2,6-dimethyl phenol; 4-n-propyl phenol; 4-n-butyl phenol; 4-n-amyl phenol; 4-tert-amyl phenol; 4-n hexyl phenol; 4-n-heptyl phenol; mono- and poly-alkyl and aromatic halophenols; p-chloroplienol; methyl p-chlorophenol; ethyl p-chlorophenol; n-propyl p-chlorophenol; n-butyl p-chlorophenol; n-amyl p-chlorophenol; sec-amyl p-chlorophenol; n-hexyl p chlorophenol; cyclohexyl p-chlorophenol; n-heptyl p-chlorophenol; n-octyl; p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benxyl-methyl p-chlorophenol; o-benzyl-m,m-dimethyl p-chlorophenol; o-phenylethyl p-chlorophenol; o-phenylethyl-m-methyl p-chlorophenol; 3-methyl p-chlorophenol 3,5-dimethyl p-chlorophenol, 6-ethyl-3-methyl p-chlorophenol, 6-n-propyl-3-methyl p-chlorophenol; 6-iso-propyl-3-methyl p-chlorophenol; 2-ethyl-3,5-dimethyl p-chlorophenol; 6-sec-butyl-3-methyl p-chlorophenol; 2-iso-propyl-3,5-dimethyl p-chlorophenol; 6-diethylmethyl-3-methyl p-chlorophenol; 6-iso-propyl-2-ethyl-3-methyl p-chlorophenol; 2-sec-amyl-3,5-dimethyl p-chloropheno I; 2-diethylmethyl-3,5-dimethyl p-chlorophenol; 6-sec-octyl-3-methyl p-chlorophenol; p-chloro-m-cresol p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; tert-amyl o-bromophenol; n-hexyl o-bromophenol; n-propyl-m,m-dimethyl o-bromophenol; 2-phenyl phenol; 4-chloro-2-methyl phenol; 4-chloro-3-methyl phenol; 4-chloro-3,5-dimethyl phenol; 2,4-dichloro-3,5-dimethylphenol; 3,4,5,6-tetabromo-2 methylphenol; 5-methyl-2-pentylphenol; 4-isopropyl-3-methylphenol; para-chlorometaxylenol (PCMX); chlorothymol; phenoxyethanol; phenoxyisopropanol; and 5-chloro-2-hydroxydiphenylmethane.

Resorcinol and its derivatives can also be used as or biocidal agents and biostatic agents. Specific resorcinol derivatives include, but are not limited to: methyl resorcinol; ethyl resorcinol; n-propyl resorcinol; n-butyl resorcinol; n-amyl resorcinol; n-hexyl resorcinol; n-heptyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro-2,4-dihydroxydiphenyl methane; 4'-chloro-2,4-dihydroxydiphenyl methane; 5-bromo-2,4-dihydroxydiphenyl methane; and 4'-bromo-2,4-dihydroxydiphenyl methane.

Examples of bisphenolic agents include, but are not limited to: 2,2'-methylene bis-(4-chlorophenol); 2,4,4'-trichloro-2' hydroxy-diphenyl ether, which is sold by Ciba Geigy, Florham Park, N.J. under the tradename TRICLOSAN; 2,2' methylene bis-(3,4,6-trichlorophenol); 2,2'-methylene bis(4-chloro-6-bromophenol); bis-(2-hydroxy 3,5-dichlorophenyl) sulphide; and bis-(2-hydroxy-5-chlorobenzyl)sulphide.

Examples of benzoic esters (parabens) include, but are not limited to: methylparaben; propylparaben; butylparaben; ethylparaben; isopropylparaben; isobutylparaben; benzylparaben; sodium methylparaben; and sodium propylparaben.

Examples of halogenated carbanilides include, but are not limited to: 3,4,4' trichlorocarbanilides, such as 3-(4-chlorophenyl)-1-(3,4-dichlorphenyl)urea sold under the tradename Triclocarban by Ciba-Geigy, Florham Park, N.J.; 3-trifiuoromethyl-4,4' dichlorocarbanilide; and 3,3',4-trichlorocarbanilide. Specific polymeric antiviral and antimicrobial agents that can be used in the invention include, but are not limited to: polyhexamethylene biguanide hydrochloride; and poly (iminoimidocarbonyl iminoimidocarbonyl iminohexamethylene hydrochloride), which is sold under the tradename Vantocil IB.

Examples of thiazolines include, but are not limited to that sold under the tradename Micro-Check; and 2-n-octyl-4-isothiazolin-3-one, which is sold under the tradename VINYZENE IT-3000 DIDP. Specific trichloromethylthioimides that can be used in the invention include, but are not limited to: N-(trichloromethylthio)phthalimide, which is sold under the tradename Fungitrol; and N-trichloromethylthio-4-cyclohexene-1,2-dicarboximide, which is sold under the tradename Vancide.

Examples of natural antimicrobial agents that can be used in the invention include, but are not limited to, oils of: anise; lemon; orange; rosemary; wintergreen; thyme; lavender; cloves; hops; tea tree; citronella; wheat; barley; lemongrass; cedar leaf; cedarwood; cinnamon; fieagrass; geranium; sandalwood; violet; cranberry; eucalyptus; vervain; peppermint; gum benzoin; basil; fennel; fir; balsam; menthol; ocmea origanuin; hydastis; carradensis; *Berberidaceac daceae; Ratanhiae Zanga*; and *Curcuma Zanga*. Also included in this class of natural antimicrobial agents are the key chemical components of the plant oils which have been found to provide antimicrobial benefit. These chemicals include, but are not limited to: anethol; catechole; camphene; thymol; eugenol; eucalyptol; ferulic acid; farnesol; hinokitiol; tropolone; limonene; menthol; methyl salicylate; carvacol; terpineol; verbenone; berberine; ratanhiae extract; caryophellene oxide; citronellic acid; curcumin; nerolidol; and geraniol.

Examples of metal salts that can be used in the invention include, but are not limited to, salts of metals in groups 3a-5a, 3b-7b, and 8 of the periodic table. Specific examples of metal salts include, but are not limited to, salts of: aluminum; zirconium; zinc; silver; gold; copper; lanthanum; tin; mercury; bismuth; selenium; strontium; scandium; yttrium; cerium; praseodymiun; neodymium; promethum; samarium; europium; gadolinium; terbium; dysprosium; holmium; erbium; thalium; ytterbium; lutetium; and mixtures thereof. A preferred metal-ion based antimicrobial agent is sold under the tradename HEALTHSHIELD, and is manufactured by HealthShield Technology, Wakefield, Mass.

Examples of broad-spectrum antimicrobial agents that can be used in the invention include, but are not limited to, those that are recited in other categories of antiviral or antimicrobial agents herein. Additional antiviral or antimicrobial agents that can be used in the processes and materials of the invention include, but are not limited to: pyrithiones, and in particular pyrithione-including zinc complexes such as that sold under the tradename Octopirox; dimethyldimethylol hydantoin, which is sold under the trade name Glydant; methylchloroisothiazolinone/methylisothiazolinone, which is sold under the tradename Kathon CG; sodium sulfite; sodium bisulfite; imidazolidinyl urea, which is sold under the tradename Germall 115; diazolidinyl urea, which is sold under the tradename Germall 11; benzyl alcohol v2-bromo-2-nitropropane-1,3-diol, which is sold under the tradename BRONOPOL; formalin or formaldehyde; iodopropenyl butylcarbamate, which is sold under the tradename POLYPHASE P100; chloroacetamide; methanamine; methyldibromonitrile glutaronitrile (1,2-dibromo-2,4-dicyanobutane), which is sold under the tradename Tektamer; glutaraldehyde; 5 bromo-5-nitro-1,3-dioxane, which is sold under the tradename Bronidox; phenethyl alcohol; o-phenylphenollsodium o-phenylphenol sodium hydroxymethylglycinate, which is sold under the tradename Suttocide A; polymethoxy bicyclic oxazolidine; which is sold under the tradename Nuosept C; dimethoxane; thimersal; dichlorobenzyl alcohol; captan; chlorphenenesin; dichlorophene; chlorbutanol; glyceryl laurate; halogenated diphenyl ethers; 2,4,4'-trichloro-2'-hydroxy-diphenyl ether, which is sold under the tradename TRICLOSAN and is available from Ciba-Geigy, Florham Park, N.J.; and 2,2' dihydroxy-5,5'-dibromo-diphenyl ether.

Additional antiviral and antimicrobial agents that can be used in the materials and methods of the invention include those disclosed by U.S. Pat. Nos. 3,141,321; 4,402,959; 4,430,381; 4,533,435; 4,625,026; 4,736,467; 4,855,139; 5,069,907; 5,091,102; 5,639,464; 5,853,883; 5,854,147; 5,894,042; and 5,919,554, all of which are incorporated herein by reference.

It is further contemplated that cell-sensitizing compositions including poly(ethylene oxide)-poly(propylene oxide) copolymer described herein can render over-the-counter consumables such as mouthwash, toothpaste, and topical ointments more effective in decreasing biological flora.

In addition, the copolymers described herein have the ability to form gels in situ, making them useful for drug delivery either alone or in combination with other drug delivery formulations. The bioactive copolymers (e.g., pluronics) can be used not only in a biodegradeable and implantable system to deliver drugs, thermoactive agents, radionucleotides, or other biologics but would also augment their desired effects through sensitization as described above.

Therefore, another aspect of the present invention provides a method of treating a microbial infection in a subject. The method includes administering to the subject an antimicrobial agent and an amount of a cell-sensitizing composition including a poly(ethylene oxide)-poly(propylene oxide) copolymer effective to potentiate the biocidal or biostatic properties of the antimicrobial agent.

In one aspect, a poly(ethylene oxide)-poly(propylene oxide) copolymer composition can be administered to a subject concomitantly with an oral antibiotic pharmaceutical composition, wherein the amount of poly(ethylene oxide)-poly(propylene oxide) copolymer composition is effective in potentiating the biocidal or biostatic of the oral antibiotic therapy.

Antibiotic agents administered in conjunction with a poly(ethylene oxide)-poly(propylene oxide) copolymer composition can include, but are not limited to aminosalicylic acid, nalidixic acid, amoxicillin, amoxicillin and potassium clavulanate, ampicillin, ampicillin and sulbactam, azithromycin, bacampicillin, carbenicillin indanyl sodium (and other carbenicillin salts), capreomycin, cefadroxil, cefazolin, cephalexin, cephalothin, cephapirin, cefaclor, cefprozil, cephadrine, cefamandole, cefonicid, cefibuten, ceftizoxime, ceftriaxone, cefepime, cefinetazole, cefotetan, cefoxitin, ciprofloxacin, clarithromycin, clindamycin, clofazimine, cloxacillin, co-trimoxazole, cycloserine, dicloxacillin, dirithromycin, erythromycin (and erythromycin salts such as estolate, ethylsuccinate, gluceptate, lactobionate, stearate), ethambutol-HCl and other salts, ethionamide, fosfomycin, imipenem, isoniazid, levofloxacin, lomefloxacin, loracarbef, methicillin, methenamine, metronidazole, mezlocillin, nafcillin, nitrofurantoin, norfloxacin, novobiocin, ofloxacin, oxacillin, penicillin V, penicillin salts, penicillin complexes, pentamidine, piperacillin, piperacillin and tazobactam, sparfloxacin, sulfacytine, sulfamerazine, sulfamethazine, sulfamethizole, sulfasalazine, sulfisoxazole, sulfapyrazine, sulfadiazine, sulfinethoxazole, sulfapyridine, ticarcillin, ticarcillin and potassium clavulanate, trimethoprim, trimetrexate, troleandomycin, vancomycin and mixtures thereof.

Poly(ethylene oxide)-poly(propylene oxide) copolymer compositions may also be used to coat medical/surgical devices and permanent medical/surgical implants with bioactive poly(ethylene oxide)-poly(propylene oxide) copolymer compositions and control poly(ethylene oxide)-poly(propylene oxide) copolymer composition release.

Percutaneous devices (such as catheters) and implanted medical devices (including, but not limited to, pacemakers, vascular grafts, stents, and heart valves) commonly serve as foci for microbial (e.g., bacterial and fungal) infection. The tendency of some microorganisms (e.g., *Staphylococcus* bacteria) to adhere to and colonize the surface of the device, promotes such infections, which increase the morbidity and mortality associated with use of the devices. Therefore, in another aspect, poly(ethylene oxide)-poly(propylene oxide) copolymer compositions or pharmaceutical compositions thereof can be used to treat or prevent microbial infection on a medical device by contacting the device with an antimicrobial agent and an poly(ethylene oxide)-poly(propylene oxide) copolymer composition or pharmaceutical composition thereof in an amount effective to potentiate the antimicrobial agent.

A medical device can include any instrument, implement, machine, contrivance, implant, or other similar or related article, including a component or part, or accessory which is recognized in the official U.S. National Formulary the U.S. Pharmacopoeia, or any supplement thereof; intended for use in the diagnosis of disease or other conditions, or in the cure, mitigation, treatment, or prevention of disease, in humans or in other animals; or, intended to affect the structure or any function of the body of humans or other animals, and which does not achieve any of its primary intended purposes through chemical action within or on the body of human or other animal, and which is not dependent upon being metabolized for the achievement of any of its primary intended purposes.

A medical device can include, for example, endovascular medical devices, such as intracoronary medical devices. Examples of intracoronary medical devices can include stents, drug delivery catheters, grafts, and drug delivery balloons utilized in the vasculature of a subject. Where the medical device comprises a stent, the stent may include peripheral stents, peripheral coronary stents, degradable coronary stents, non-degradable coronary stents, self-expanding stents, balloon-expanded stents, and esophageal stents. The medical device may also include arterio-venous grafts, by-pass grafts, penile implants, vascular implants and grafts, intravenous catheters, small diameter grafts, surgical mesh, artificial lung catheters, electrophysiology catheters, bone pins, suture anchors, blood pressure and stent graft catheters, breast implants, benign prostatic hyperplasia and prostate cancer implants, bone repair/augmentation devices, breast implants, orthopedic joint implants, dental implants, implanted drug infusion tubes, oncological implants, pain management implants, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, biliary drainage products, dialysis catheters, central venous access catheters, and parental feeding catheters.

The medical device may additionally include either arterial or venous pacemakers, vascular grafts, sphincter devices, urethral devices, bladder devices, renal devices, gastroenteral and anastomotic devices, vertebral disks, hemostatic barriers, clamps, surgical staples/sutures/screws/plates/wires/clips, glucose sensors, blood oxygenator tubing, blood oxygenator membranes, blood bags, birth control/IUDs and associated pregnancy control devices, cartilage repair devices, orthopedic fracture repairs, tissue scaffolds, CSF shunts, dental fracture repair devices, intravitreal drug delivery devices, nerve regeneration conduits, electrostimulation leads, spinal/orthopedic repair devices, wound dressings, embolic protection filters, abdominal aortic aneurysm grafts and devices, neuroaneurysm treatment coils, hemodialysis devices, uterine bleeding patches, anastomotic closures, aneurysm exclusion devices, neuropatches, vena cava filters, urinary dilators, endoscopic surgical and wound drainings, bandages, surgical tissue extractors, transition sheaths and dialators, coronary and peripheral guidewires, circulatory support systems, tympanostomy vent tubes, cerebro-spinal fluid shunts, defibrillator leads, percutaneous closure devices, drainage tubes, bronchial tubes, vascular coils, vascular protection devices, vascular intervention devices including vascular filters and distal support devices and emboli filter/entrapment aids, AV access grafts, surgical tampons, and cardiac valves.

The medical device can be formed of any suitable material known in the art including, for example, biocompatible polymers, such as PTFE, ePTFE, poly(ethylene co-vinyl alcohol) (pEVOH) and silicone, metals and metal alloys, such as gold, NITINOL, NiTi and titanium, and glass. Other examples of suitable biocompatible polymers can include polyalkylene oxides, polymethacrylates, polyurethanes, cellulosics, polyhydroxyalkyl acrylates, polyesters, and polymers comprised of at least one polyethylene monomer, such as polyethylene glycol (PEG) or polyethylene oxide, polymers comprised of polyamine monomers, such as polyethyleneimine (PEI), and poly(L-lactide) (PLLA), poly-p-dioxanone (PDO), polycaprolactone (PCL), polyvinyl alcohol (PVA), and poly(lactide-co-glycolide) (PLG).

The following examples are for the purpose of illustration only and are not intended to limit the scope of the claims, which are appended hereto.

Example 1

This Example shows the effect of various Pluronics (L10, L61, L64, P85) combined with hyperthermia (45° C.) and low-grade hyperthermia (43° C.) on ATP depletion, cell death, and expression of Hsp70.
Materials and Methods
Formulation of Pluronic Solutions Pluronics L10, L61, L64, and P85 (molecular weight (Mw) of 3200, 2000, 2900, and 4600 Da, and PPO/PEO units of 49.7/7.3, 31/4.55, 30/26.36, and 39.66/52.27, respectively [36]) were used. Pluronic P85 and L61 were generously donated by BASF (Shreveport, La.). Pluronic L10 and L64 were purchased from Sigma Aldrich (Milwaukee, Wis.). Pluronic stock solutions were prepared by dissolving each polymer in RPMI medium overnight at 4° C. at concentrations of 10 mg/mL, 0.3 mg/mL, 0.5 mg/mL, and 3 mg/mL for P85, L61, L64, and L10 respectively. The optimum doses of Pluronic were obtained based on the mitochondrial succinate dehydrogenase (WST-1) assay. Solutions were filtered with a sterile 0.22 μm syringe filter (Millipore, Mass.) and test solutions stored at 4° C. until use.
Cell Culture Rat DHD/K12/TRb colorectal adenocarcinoma cells (European Collection of Cell Cultures, Salisbury, UK) originating from 1,2-dimethylhydrazine induced colon adenocarcinoma in BDIX rats, were cultured in complete RPMI 1640 (10% fetal bovine serum, 1% penicillin/streptomycin (Invitrogen, Carlsbad, Calif.). Cells were cultured at 37° C. and 5% $CO_2$ in a humidified atmosphere. Cells were passaged at 90% confluence. Cells were detached with 0.25% trypsin-EDTA 24 h before treatment and plated onto flat bottom, tissue culture-treated, opaque walled, 96-well plates with $2 \times 10^4$ cells in each well.
Cell Treatment After 24 h of incubation, medium was aspirated and cells were incubated with 100 μL of Pluronic test solutions (10 mg/mL, 0.3 mg/mL, 0.5 mg/mL, 3 mg/mL for P85, L61, L64, and L10) for 20 min at 37 μC. For Pluronic plus low-grade hyperthermia treatment, cells were exposed to Pluronic test solutions as above and received 43° C. for 20 min. At the endpoint, test solutions were removed, cells were washed with incomplete RPMI and wells were replenished with complete RPMI. Plates were returned to a 37° C. humidified incubator for a set time and analyzed as described below.
In Vitro Cell Viability Changes in ATP levels were measured using a standard luciferin-luciferase assay (CELLTITER-GLO luminescent cell viability assay, Promega, Madison, Wis.). This assay measures the luminescence resulting from the ATP-driven luciferase/luciferin reaction. The measured signal corresponds to the relative amount of ATP in those cells and is also proportional to the number of living cells. After Pluronic and/or low-grade hyperthermia treatment at 37° C. or 43° C. (±0.05° C.) for 20 min, 100 μL of reagent was added to each well. The plates were shaken for 2 min to promote cell lysis, and relative luminescence was measured using a plate reader (Tecan, Durham, N.C.). At the same time points, cells were trypsinized and a single cell suspension was obtained by well mixing with a pipette. The cell suspension was mixed with 0.4% trypan blue in 1:1 ratio and after ~3 min viable cells were counted using a haemocytometer (Fisher Scientific, Pittsburgh, Pa.). All studies were repeated in triplicate.
Protein Analysis Cells were treated with heat (43°±0.05° C.) with or without Pluronic for 20 min. At different time points (0, 2, 4, 6, 9, 24, 48, 72 h post treatment), cells were lysed on ice for 30 min in a lysis buffer (Cell Signaling Technology, Beverly, Mass.) containing a protease inhibitor cocktail (Dimethyl sulphoxide, benzenesulphonylfluoride, trypsin inhibitor, bestatin, leucine, pepstatin A) (Sigma, Mo.) and centrifuged at 10,000 g for 10 min at 4° C. A Bio-Rad (Hercules, Calif.) protein assay kit was used to determine protein concentration in the supernatant. Protein was electrophoresed on sodium dodecyl sulphate/polyacrylamide gels and transferred to nitrocellulose membranes. Membranes were blocked with 5% nonfat dry milk in TBST buffer (0.1% Tween-20, 20 mM of Tris-HCl; pH 7.5, and 140 mM of NaCl). Membranes were then incubated with primary antibodies against Hsp70 and β-actin (Assay Designs/Stressgen, Ann Arbor, Mich.), followed by secondary antibody/horseradish peroxidase conjugates (Pierce, Ill.). The SNAP i.d. system (Millipore, Mass.) was used for the antibody incubation. Horseradish peroxidase (HRP) substrate-luminal reagent (Millipore, Mass.) was used to detect chemiluminescence signal and photographed by Alpha Imager HP (Cell Biosciences (proteinsimple), Santa Clara, Calif.).

For in vivo Hsp70 analysis, tumors were excised from each group of BDIX rats and tissue samples were prepared by homogenizing the piece of dissected tumor (radially sectioned) in lysis buffer, followed by centrifugation at 4° C. and collecting the supernatant. Western blot analysis was carried out as described above.

In Vivo Assessment of Hsp70 Analysis

BDIX rats 12 weeks old carrying subcutaneous tumors were used in this study. Tumors were created by injecting $1.0 \times 10^5$ rat colorectal adenocarcinoma cells (DHD/K12/TRb). The tumors were treated with a combination of L61 pretreatment and hyperthermia. L61 was chosen for these experiments because it had demonstrated sensitizing efficacy in previous studies in the same rodent model of cancer (unpublished data). Therefore, in this study we used L61 for in vivo analysis of Hsp70.

After 5 weeks the rats were randomly divided into three groups. Animals were anaesthetized using 1% isoflurane with an oxygen flow rate of 1 L/min (EZ150 Isoflurane Vaporizer; EZ Anesthesia, Palmer, Pa.). The first group received 0.1 mg/mL of L61 in saline intravenously. Four hours after L61 treatment, the tumors were subjected to hyperthermia at 45° C. for 2 min with an abdominal grounding pad. Application of local hyperthermia was performed using a 480-kHz RF generator (Radionics, Burlington, Mass.) and a custom-designed 21-gauge monopolar needle electrode. The other group received the same amount of saline instead of L61 followed by hyperthermia at 45° C. for 2 min. The control group received only saline. The animals were euthanized 5 h after hyperthermia and tumors were excised and stored at −80° C. for Hsp70 analysis.

Results

Effect of Pluronic on ATP Recovery and Cell Growth In Vitro

The effects of low-grade hyperthermia alone, Pluronic treatment alone, and combined treatment of heat plus Pluronic on ATP depletion are shown in FIG. 1. The data is normalized to the untreated control and reported as a percentage (n=3). Subsequent to heating at 43°±0.05° C. for 20 min, ATP decreased to 85%±15.5% (P=0.18) relative to the untreated control. Twenty-four hours after low-grade hyperthermia alone, ATP recovered to 96%±4.5% (P=0.18). ATP decreased immediately after Pluronic treatment to 62%±19%, 63%±6%, and 78%±3% (P<0.03) of untreated control for L10, L61, and L64 respectively. Parallel to the heat alone treatment, after 24 h, ATP of Pluronic-treated cells recovered gradually to 100%±7%, 96%±2%, and 94%±7% (P<0.3). A significant loss of cell viability was observed when cells were treated with both low-grade hyperthermia and Pluronic. The synergic treatments with L10 demonstrated significant ATP depletion compared to the treatments with other Pluronic polymers used in this study reaching a level of less than half of the untreated control and heat alone treatments immediately after L10 plus low-grade hyperthermia treatment (42%±13%, P=0.002 and 37%±8%, P=0.02). Five hours after treatment, ATP returned to 67%±18% (P<0.05) of untreated control, demonstrating a high production of energy. Subsequently, 24 h after treatment, the ATP level decreased to 8%±4% (P<0.001) of untreated control.

The amount of ATP after the synergic treatment of L61 and L64 plus low-grade hyperthermia displayed similar behavior to the L10 with a drop of ATP to 67%±18% (P=0.03) and 50%±10% (P<0.01) of heat alone, respectively, and a slight increase was observed within 5-10 h. However, in contrast to L10, ATP recovered to 64%±4% (P<0.001) and 66%±18% (P=0.08) of untreated control after 24 h for L61 and L64, respectively.

Figure 2:
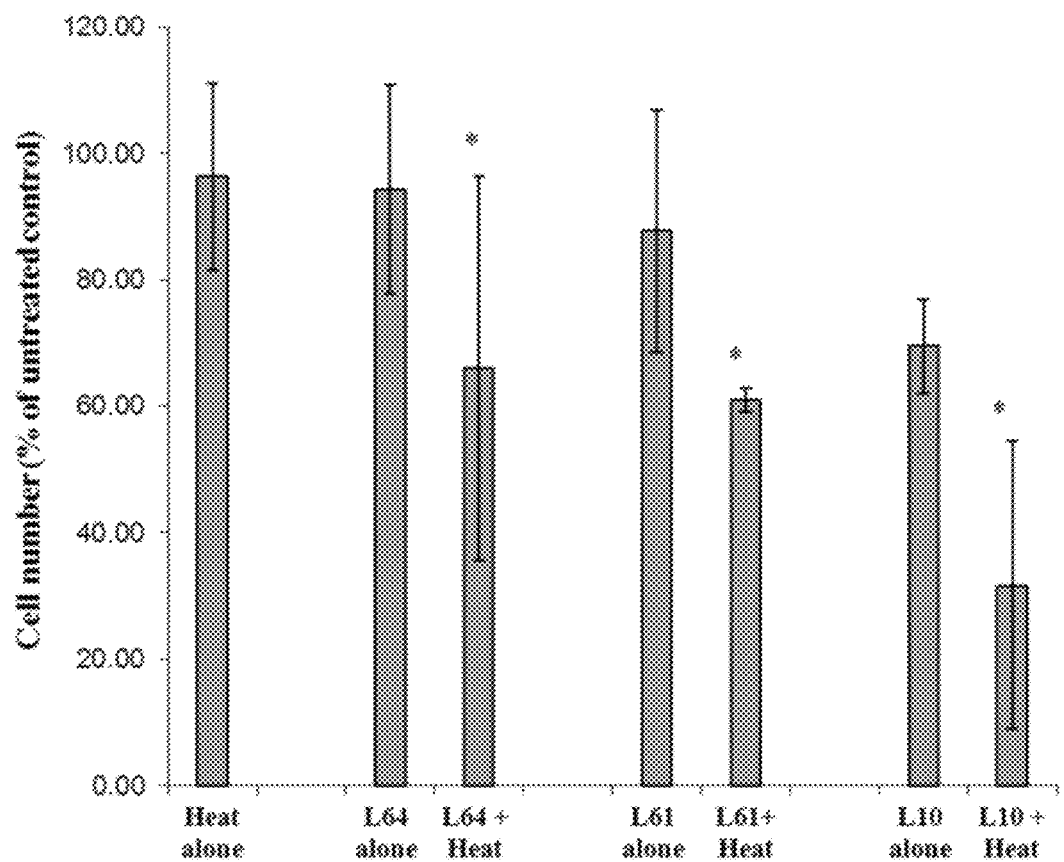
FIG. 2 illustrates a table showing relative viable cell number 72 h following treatment with heat (43°±0.05° C. for 20 min), Pluronic L10, L61, L64 alone and Pluronic+heat. Cell counts were normalized to the untreated control (n=3). *Indicates significant difference compared to control (P<0.05).

Pluronic effect on cell proliferation was investigated 72 h after treatment and is presented in FIG. 2. Cells treated with heat alone or with L64, L61, and L10 showed proliferation levels of 96%±14%, 94%±16%, 87%±19%, 69%±7% (P<0.001) of untreated control respectively. In contrast, when combined with heat, the number of live cells decreased to 68%±25%, 63%±7%, and 33%±10% (P<0.05) for L64, L61, and L10 respectively.

Effect of Pluronic on Heat Shock Protein 70 Expression In Vitro

Figure 3:
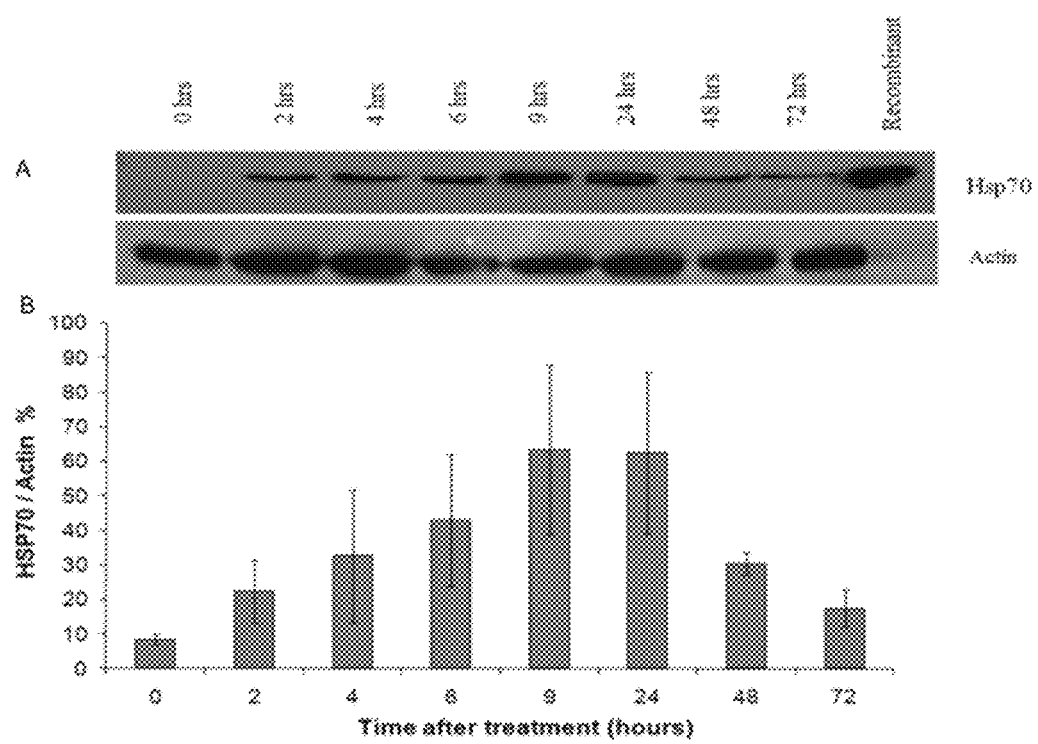
FIG. 3 illustrates: (A) a western blot showing up-regulation of Hsp70 expression in DHD/K12/TRb cells treated with 43° C. low-grade hyperthermia for 20 min; and (B) a table showing Hsp70 expression at different time points normalized versus actin.

Hsp70 expression in confluent DHD/K12/TRb monolayer cells after low-grade hyperthermia treatment (43°±0.05° C.) was determined by immunoblot analysis. After 20 min of heat exposure, cells were returned to the 37° C. incubator and, at different time points, cell lysates were collected and analyzed for Hsp70. FIG. 3 shows the heat-induced increase in Hsp70 protein expression at different post treatment time points (n=3). The Hsp70 expression was up-regulated to a detectable level (38%±6% of actin, P<0.05) within 2 h after heat treatment alone. Maximal Hsp70 expression (80%±23% of actin amount, P<0.05) was detected between 9 and 24 h after treatment and decreased gradually afterwards for up to 72 h.

Figure 4:
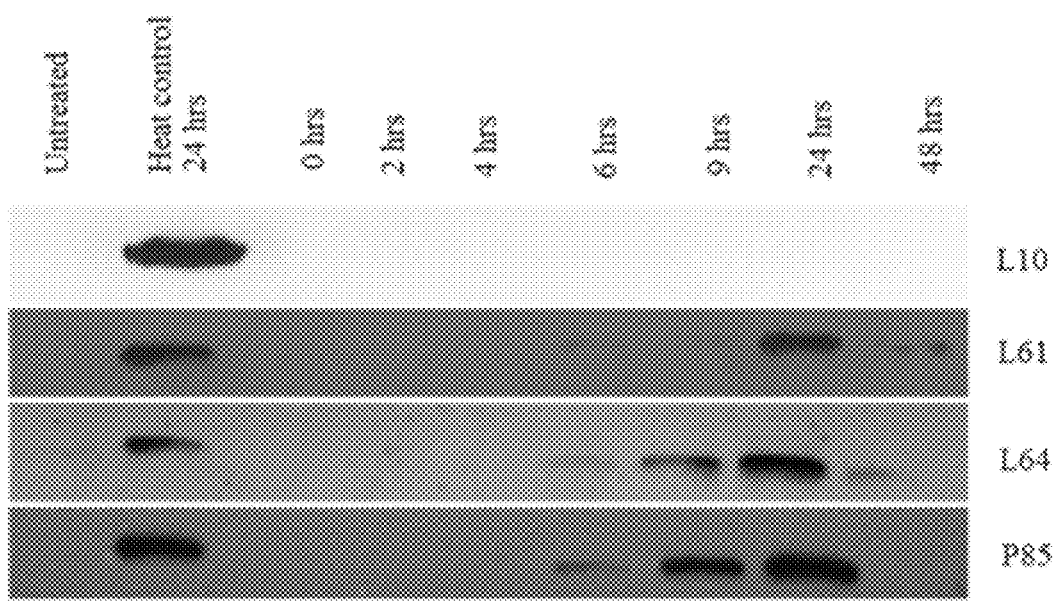
FIG. 4 is a western blot showing inhibition of Hsp70 expression in DHD/K12/TRb cells treated with different Pluronics and 43° C. low grade hyperthermia for 20 min.
Figure 5:
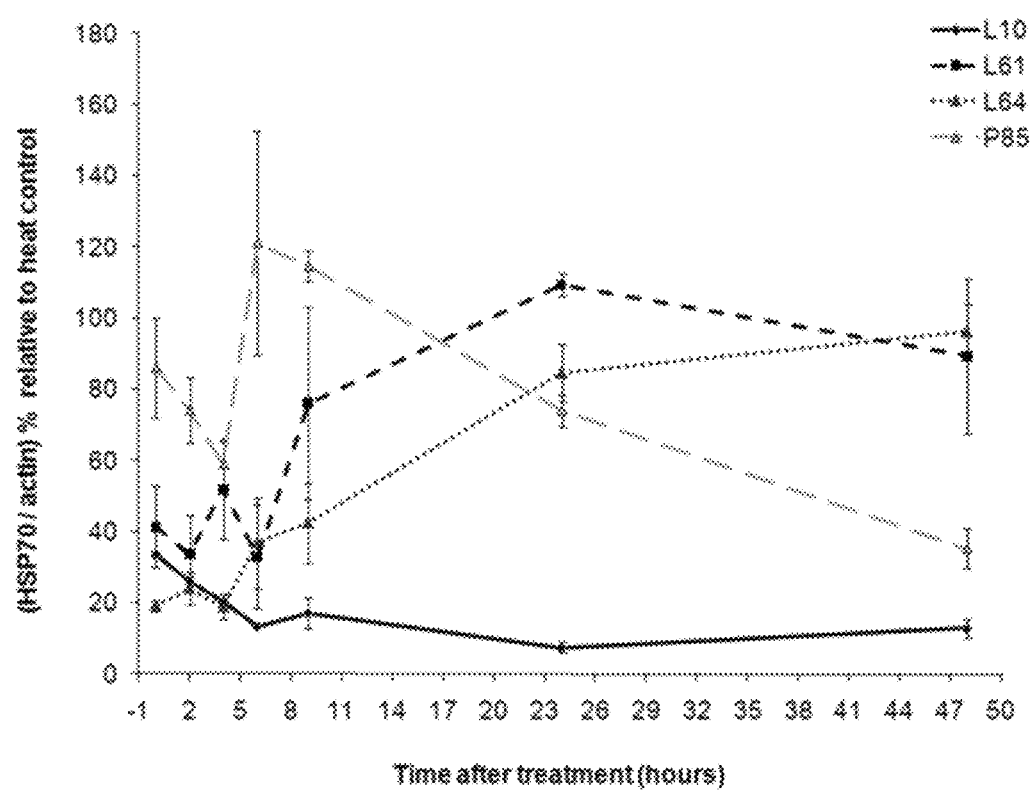
FIG. 5 illustrates a plot showing the effect of Pluronic L10, L61, L64, and P85 on the inhibition of Hsp70 with the hyperthermia treatment at 43° C. for 20 min. The peaks are normalized to actin and calculated as a percentage relative to heat only treatment at same time points.
Figure 6:
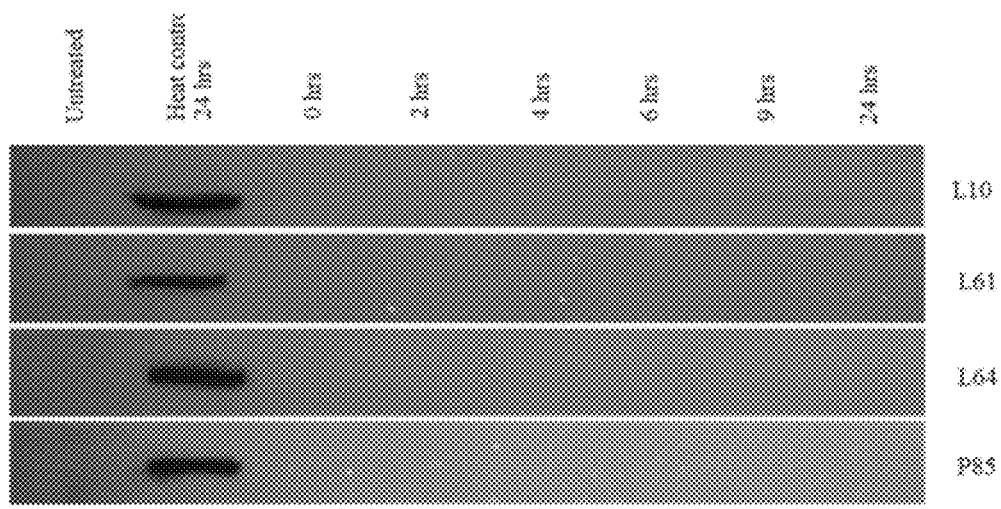
FIG. 6 is a western blot showing expression of Hsp70 in DHD/K12/TRb cells treated with Pluronic L10, L61, L64, or P85 for 20 min at 37° C.

Low-grade hyperthermia combined with Pluronic decreased Hsp70 expression (FIG. 4). Pluronic L10 and low-grade hyperthermia completely suppressed Hsp70 expression (n=3). Here, the 'heat control' is defined as the Hsp70 expression of heat only treatment at the same time points. Pluronic L61 and L64 synergic treatment resulted in suppression of Hsp70 for up to 6 h. After 6 h, Hsp70 expression returned to a detectable level. A less remarkable inhibition of Hsp70 protein was noted with Pluronic P85. In all cases, the corresponding β-actin analysis was conducted (figures are not shown) and each band normalized to β-actin. FIG. 5 and Table I summarize the Pluronics' effects on Hsp70 expression compared to those of the heat control. Finally, FIG. 6 shows the representative immunoblot outcome for Hsp70 analysis of Pluronic-only treatments for cancer cells. The results showed that there was an insignificant increase of intracellular Hsp70 expression compared to the heat control.

TABLE I

Table I. Summary of Hsp70 expression following treatment with low-grade hyperthermia in conjunction with Pluronic.

| Treatment | Time to intial Hsp70 expression (h) | Initial Hsp70 expression (% actin) | Time of maximum Hsp70 expression (h) | Maximum Hsp70 expression (% actin) |
|---|---|---|---|---|
| Heat alone | 2 | 38 ± 6 | 24 | 80 ± 23 |
| L10 + heat | 48 | 9 ± 1 | 48 | 14 ± 4 |
| L61 + heat | 6 | 19 ± 14 | 24 | 87 ± 3 |
| L64 + heat | 6 | 21 ± 12 | 24 | 68 ± 8 |
| L85 + heat | 6 | 70 ± 5 | 9 | 92 ± 6 |

Data are mean of 3 with the ± STDEV.
*Hsp70 expression is significantly different from the expression of heat control with P < 0.05.
**Hsp70 expression is significantly different from the expression of heat control with P < 0.001/

In Vivo Expression of Hsp70

Figure 7:
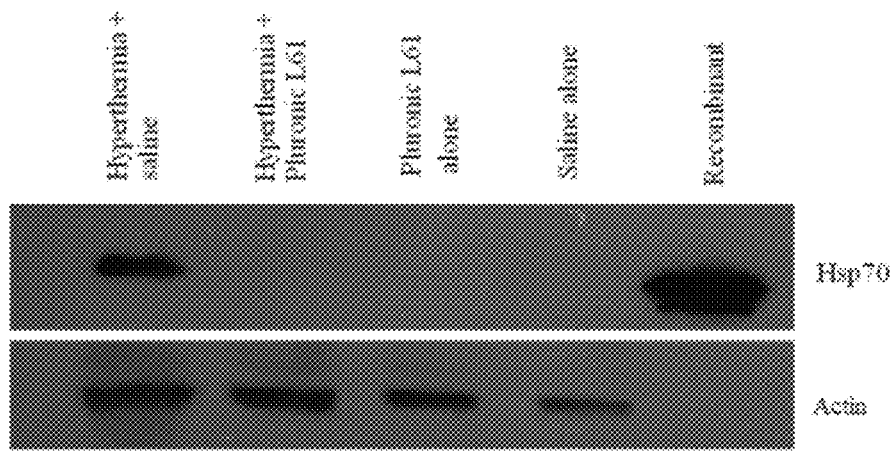
FIG. 7 is a western blot showing Hsp70 expression 5 h after hyperthermia (for 20 min at 45° C.) in subcutaneous colorectal tumor model.

In vivo Hsp70 expression in hyperthermia-treated tumors with or without Pluronic L61, and subsequent control groups are shown in FIG. 7. Hsp70 expression in the L61 pretreated with hyperthermia group (n=8), the L61 alone group (n=3), and the saline treated group (n=2) were undetectable. An average of 88%±10% (normalized to constitutively expressed β-actin) Hsp70 expression was observed in tumors, 5 h after hyperthermia alone treatment.

Example 2

In this example we show how Pluronic structure affects its ability to sensitize cancer cells to hyperthermia.
Materials and Methods
Materials Pluronic P85 ($EO_{26}$-$PO_{40}$-$EO_{26}$) and L61 ($EO_2$-$PO_{30}$-$EO_2$) were generously donated by BASF Corporation (Florham Park, N.J.). All other Pluronic copolymers were purchased from Sigma Aldrich (Milwaukee, Wis.). Table 2 summarizes the properties of all Pluronic polymers used in these studies. Trypsin-EDTA, Dulbecco's phosphate buffered saline (DPBS, without calcium or magnesium), RPMI medium 1640 (with L-glutamine and with phenol red), and penicillin/streptomycin were purchased from Gibco (Grand Island, N.Y.). Fetal bovine serum (FBS) was purchased from Hyclone (Logan, Utah). DispoDialyzer system (SPECTRA/POR) and sterile 0.22 mm syringe driven filter units (MillexTM-GP) and opaque-walled 96-well cell culture plates were purchased from Fisher Scientific (Pittsburgh, Pa.). The Caspase-Glo 3/7 assays were purchased from Promega (Madison, Wis.).

TABLE 2

Pluronic information

| Pluronic | Formula[a] | Mw (Da)[b] | HLB[c] | CMC (M)[d] | CMC (wt %)[d] |
|---|---|---|---|---|---|
| L31 | $EO_2$-$PO_{16}$-$EO_2$ | 1100 | 3.2 | N/A | |
| L35 | $EO_{11}$-$PO_{16}$-$EO_{11}$ | 1900 | 10 | $5.3 \times 10^{-3}$ | 1.007 |
| L61 | $EO_2$-$PO_{31}$-$EO_2$ | 2000 | 2.0 | $1.1 \times 10^{-4}$ | 0.022 |
| L44 | $EO_{10}$-$PO_{23}$-$EO_{10}$ | 2200 | 8 | $3.6 \times 10^{-3}$ | 0.792 |
| L62 | $EO_6$-$PO_{35}$-$EO_6$ | 2500 | 4.0 | $4.0 \times 10^{-4}$ | 0.1 |
| L81 | $EO_3$-$PO_{43}$-$EO_3$ | 2750 | 2.0 | $2.3 \times 10^{-5}$ | 0.0063 |
| L64 | $EO_{13}$-$PO_{30}$-$EO_{13}$ | 2900 | 8.0 | $4.8 \times 10^{-4}$ | 0.14 |
| L10 | $EO_4$-$PO_{50}$-$EO_4$ | 3200 | 2.0 | N/A | |
| L92 | $EO_8$-$PO_{50}$-$EO_8$ | 3650 | 4.0 | $8.8 \times 10^{-5}$ | 0.032 |
| L121 | $EO_5$-$PO_{68}$-$EO_5$ | 4400 | 2.0 | $1.0 \times 10^{-6}$ | 0.0004 |
| P85 | $EO_{26}$-$PO_{40}$-$EO_{26}$ | 4600 | 10 | $6.5 \times 10^{-5}$ | 0.03 |
| P123 | $EO_{20}$-$PO_{69}$-$EO_{20}$ | 5750 | 6.0 | $4.4 \times 10^{-6}$ | 0.0025 |
| F87 | $EO_{61}$-$PO_{40}$-$EO_{61}$ | 7700 | 24 | $9.1 \times 10^{-5}$ | 0.07 |

[a,b]Information provided by the manufacturer; PO, propylene oxide; EO, ethylene oxide. Mw: molecular weight; Da: Dalton.
[c]Information calculated based on Mw of PO and EO; HLB: hydrophilic lipophilic balance.
[d]CMC, critical micelle concentration; information was adapted from Batrakova et al.[39]. M: molar; wt %: weight percent.

Colorectal Carcinoma Model

The DHD/K12/TRb, rat colorectal adenocarcinoma was used in these studies. This metastatic cell line originated from a 1,2-dimethylhydrazine induced colon adenocarcinoma in BDIX rats. This tumor model possesses well defined properties essential for study of metastasis of colon carcinomas, such as a reproducible pattern of in vivo behavior and the ability to be propagated both in vitro and in vivo. The cells were maintained in complete RPMI medium, containing 10% FBS and 1% (v/v) penicillin/streptomycin, in a 37° C. humidified incubator with 5% $CO_2$. For tumor propagation, all cells were from the second passage.
Cell Treatments Cells ($10^5$/mL) were seeded in 96- or 24-well plates overnight to allow adhesion. Prior to treatment, cell medium was removed and treatment solutions of Pluronics dissolved in RPMI were added to the corresponding wells (50 and 300 µL in 96- and 24-well plates, respectively). Cells were exposed to the treatment solutions for 0-20 min at 37° C. and those in the hyperthermia group were further incubated at 43° C. in a circulating water bath for 20 min. This temperature was selected to mimic the minimum sublethal hyperthermia received by tumor tissue at the periphery of the ablated volume. After treatment, the test medium was removed; cells were washed twice and replenished with 100 µL of completed RPMI. Plates were returned to the incubator. WST-1 and caspase assays (described below) were carried out at 2 and 24 h after treatment. At each of the assay times, additional plates of cells were trypsinized and viable cells counted with a haemocytometer.
WST-1 Assay Dehydrogenase activity was measured with the WST-1 (WST: water soluble tetrazolium, or 4-[3-(4-iodophenyl)-2-(4-nitrophenyl)-2H-5-tetrazolio]-1,3-benzene disulphonate) assay. This assay works based on the principle that mitochondrial succinate dehydrogenase, which becomes inactive in non-viable cells, catalyses the conversion of a soluble form of tetrazolium, a salt, to a colored dye formazan changing absorbance. Theoretically, the quantified dehydrogenase activity is directly proportional to the number of live cells. The WST-1 assay was performed 24 h after treatment following manufacturer directions. Briefly, supernatant was aspirated while reagents were diluted with completed RPMI medium. 100 µL of the diluted reagents was added to each well, plates were kept for 1 h at room temperature, and the optical density was determined at $\lambda=450$ nm using a microplate reader (ELx808, Bio-Tek, Winooski, Vt.).
CASPASE GLO 3/7 Assay Apoptosis was determined with the Promega CASPASE GLO 3/7 assay. This assay works on the principle that caspase 3 or 7, which is activated in cells undergoing apoptosis, cleaves the added luminogenic substrate releasing aminoluciferin. This luciferin molecule subsequently reacts with luciferase resulting in the production of light. Briefly, the assay reagent was prepared, and the cells in 96-well plates were removed from the incubator. Once the reagent and the plates were equilibrated to room temperature, 100 µL of the reagent was added to each of the wells after thorough mixing by vortex. Subsequently, the contents in each well were gently mixed with a plate shaker at 300 rpm for 30 s. The plate was kept at room temperature, and the luminescence was detected 1 h later with a plate reader (TECAN, Durham, N.C.).
Structure—Function Correlation For identifying the relationship between Pluronic structure and its thermosensitizing function, one concentration (2.5 mg/mL) and exposure time (20 min) were selected to simplify the experimental design. Thirteen Pluronics, L31, L35, L44, L61, L62, L81, L64, L10, L92, L121, P85, P123 and F87 were tested. Based on these data, the enzyme activities of cells treated with the copolymers were plotted against their molecular weight (Mw).
In Vivo Tumor Treatment Efficacy Studies with Pluronic L61

To demonstrate the utility of the thermosensitizing strategy in vivo, L61 was selected from our in vitro results as one of the most promising candidates. To test its efficacy in enhancing hyperthermia tumors were treated with systemic L61 in combination with RF ablation. Adult male BDIX rats, bred in-house (originally obtained from Charles River Laboratories), between 5-8 weeks old received one subcutaneous tumor inoculation on each of the upper hind legs. On the day of tumor inoculation, cells were harvested by trypsin-EDTA, washed in RPMI, centrifuged at 800 rpm for 5 min and resuspended at a final concentration of $2 \times 10^6$ cells/mL. Cells were then loaded into individual 1-mL syringes equipped with 27-gauge needles, and a separate syringe was used for each injection site. For tumor inoculation, the rats were anaesthetized with 1% isoflurane with an $O_2$ flow rate of 1 L/min (EZ150 Isoflurane Vaporizer, EZ Anesthesia™). Cell suspension (50 mL) was injected subcutaneously at each site.

At an initial tumor volume of $2502 \pm 302$ mm$^3$, rats were randomly divided into two groups. One group received 0.1 mg/kg of L61 in saline intravenously followed by RF ablation 4 h later. This pretreatment time of Pluronic L61 was based on results of our pilot study and published Pluronic in vivo half-life. The other group of rats received intravenous saline followed with RF ablation. The RF ablation protocol was as follows: ablation probe: 17-gauge, 1-cm active single tip Radionics RF probe; temperature: 90° C.; ablation duration: 3 min. Rat weight and tumor diameters (measured with calipers) were recorded weekly. The tumor volumes were estimated by:

$$v_t = \frac{a_t \cdot b_t^2}{2}$$

$a_t$ is the longest tumor diameter and $b_t$ is the perpendicular diameter.

Results

Enzyme Activity after Pluronic Exposure

Figure 8:
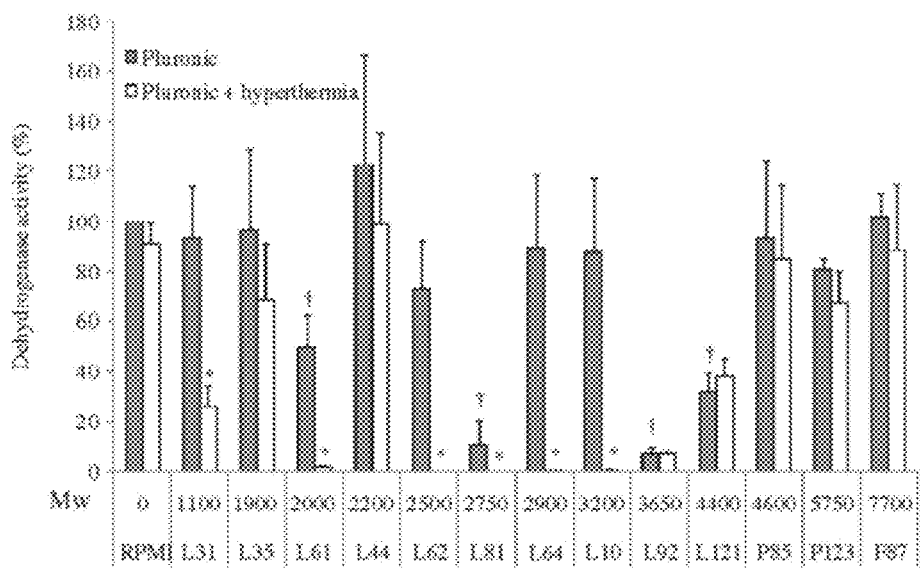
FIG. 8 illustrates a table showing Pluronic thermosensitizing effects on DHD/K12/TRb cells in vitro after 20 min of Pluronic and hyperthermia (at 43° C.) co-exposure.

Pluronic polymers L31, L61, L62, L64 and L10 in synergy with low-grade hyperthermia were able to reduce cellular enzyme activity to $25.8 \pm 8.5\%$ $0.0 \pm 1.8\%$, 0, $0.2 \pm 0.2\%$ and $0.6 \pm 0.3\%$ of the untreated control, respectively. In contrast, cells treated with Pluronic alone showed a modest change to $93.1 \pm 21.1\%$, $66.9 \pm 21.9\%$, $72.8 \pm 19.5\%$, $89.5 \pm 29.3\%$ and $87.2 \pm 30.2\%$ of the untreated control. Pluronics L81, L92 and L121 appeared to be toxic to cells at the studied dose; administered alone they reduced enzyme activity to $10.8 \pm 9.9$, $6.5 \pm 3.1$ and $32.1 \pm 7.5\%$ of the control, respectively (FIG. 8).

Figure 9:
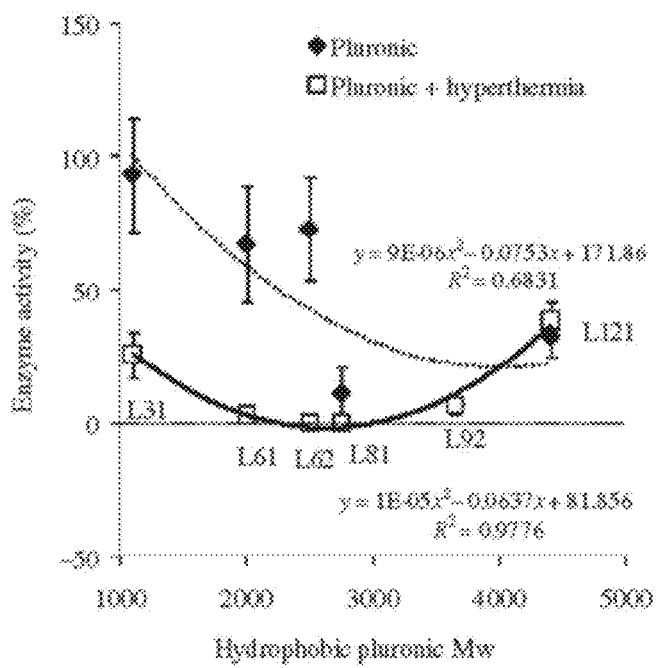
FIG. 9 illustrates a plot sowing dependence of hydrophobic Pluronic bioactivity on average molecular weight. Results are based on the dehydrogenase activity acquired with WST-1 assay.

The investigated Pluronics were divided into two groups based on their HLB. The hydrophobic polymers were defined as those with HLB between 1 and 7, and the hydrophilic polymers were defined as those with HLB above 7. Then, the cellular enzyme activities acquired with WST-1 assay from these two groups of polymers were plotted against Pluronic structural properties including $N_{PO}/N_{EO}$ ratio ($N_{PO}$: number of propylene oxide repeating units; $N_{EO}$: number of ethylene oxide repeating units), Mw, HLB and $N_{PO}$. For the hydrophilic polymers, the data did not exhibit any trends. Similarly, when cells were treated with hydrophobic Pluronics alone, no specific trends were detectable from these data. In contrast, cellular enzyme activity of cells in the hydrophobic polymer+hyperthermia treated group followed a second order polynomial function when plotted against their molecular weight (FIG. 9) with $R^2=0.98$. However, no detectable trends were observed when the enzyme activity was plotted against $N_{PO}/N_{EO}$, HLB or $N_{PO}$. Further studies are necessary to explain these observations. In summary, Pluronics with $1100 \leq Mw \leq 3200$ Da and hydrophilic lipophilic balance (HLB) between 1 to 8 were the most effective. Out of these, two Pluronics (L81, L92) lead to a drastic reduction of enzyme activity but were inherently toxic, and only one (L64) was above an HLB of 4 in this Mw range. Based on this data, we concluded that hydrophobic copolymers L31, L61, L62 and hydrophilic copolymers L64 and L10 are the most effective thermosensitizers for DHD/K12/TRb cells under the test conditions.

Cell Apoptosis in Response to Pluronic L61

Pluronic L61 was selected among the most effective polymers for further testing due to the availability of its pharmacokinetic information and its active role (in the formulation SP1049C) in a currently ongoing Phase III clinical trial for treating late stage upper gastrointestinal cancer. Apoptosis was determined with a caspase 3/7 assay. According to time-dependent characterization, caspase activity was detectable 2 h after treatment. The caspase activity was normalized by the number of viable cells per well. Results indicated that at 2 h, no significant difference in caspase activity was detected between L61 ($0.03 \pm 0.0$) treated and the untreated control ($0.05 \pm 0.01$) cells (P=0.1), while L61 in synergy with hyperthermia ($0.1 \pm 0.0$) led to an insignificant increase of caspase activity compared to L61 treated cells (P=0.07) or cells treated with hyperthermia only ($0.05 \pm 0.0$, P=0.016). Likewise, 24 h after treatment, L61 in synergy with hyperthermia caused drastic increase in caspase activity ($0.4 \pm 0.1$; P=0.005) compared to cells exposed to hyperthermia only ($0.1 \pm 0.0$). These data suggest that L61 in synergy with low-grade hyperthermia can lead to continuous apoptosis of the cells while neither treatment alone caused lethal harm to the cells.

In Vivo Efficacy with Copolymer L61

Figure 10:
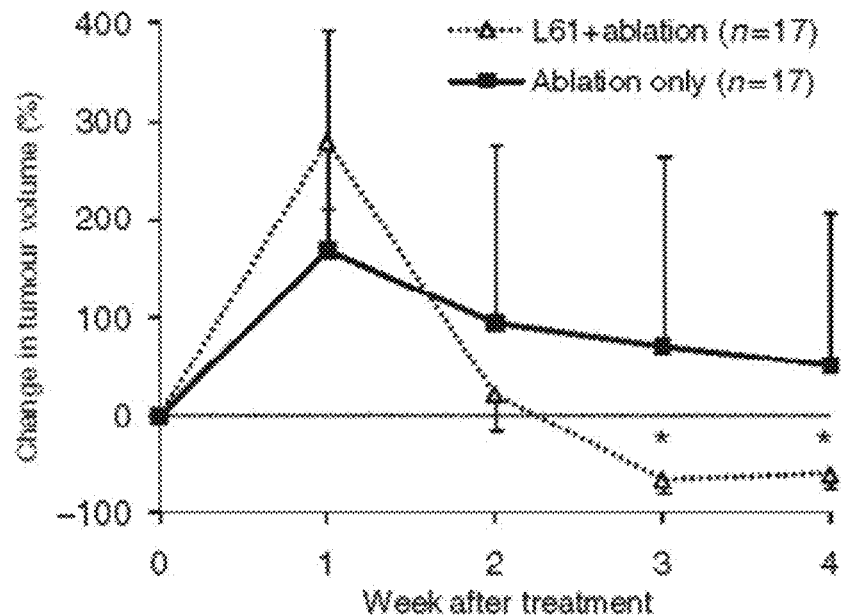
FIG. 10 illustrates a plot showing change in tumor volume relative to size before treatment in response to radiofrequency ablation with or without Pluronic L61.
Figure 11:
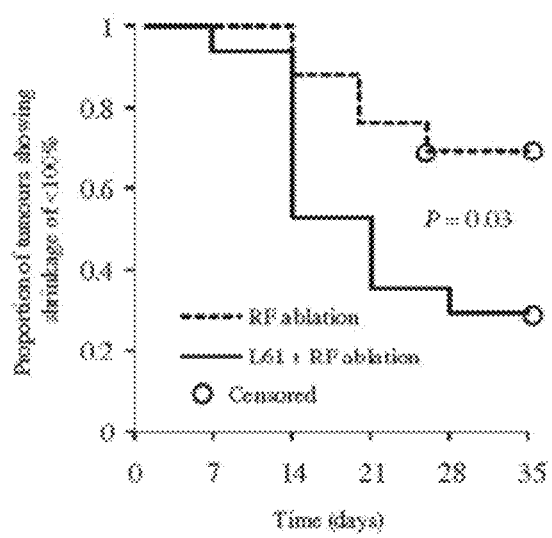
FIG. 11 illustrates a plot of the proportion of tumors showing shrinkage of less than 100% in volume.

Pluronic L61 was used in conjunction with RF ablation in treatment of colorectal carcinoma in rats. During week 1-2, no significant difference was seen in tumor progression between the RF ablation only group and the combination treatment. However, beginning at week 3 and at the conclusion of the 4-week monitoring period, the relative volume of tumors treated with a combination of L61 pretreatment and RF ablation was significantly reduced ($-60.5 \pm 55.5\%$; P=0.02) compared to those treated with RF ablation alone ($51.1 \pm 155.6\%$). More noteworthy, by physical palpation, 6/17 (35%) tumors treated with L61+RF ablation were undetectable and more than half, 9/17 (53%), of these tumors reduced in volume by more than 80%. In contrast, 3/17 (18%) of the tumors from RF ablation alone treated groups were not detectable by physical palpation and reduced in volume by more than 80% (FIG. 10). Kaplan-Meier curves were used to estimate the proportion of tumors that had not achieved a 100% reduction from baseline volume at weeks 1-4. Results from the Cox proportional hazards regression model showed that significant difference occurred between the two treatment groups with L61+RF ablation being more efficacious than RF ablation (P=0.03, FIG. 11). This analysis was repeated using a threshold of 50% reduction from baseline, and results did not differ (P=0.03).

Example 3

In this Example, the effect of Pluronic triblock copolymers (L10, L61 and L64) as sensitizing agents for radiation therapy in Gli36 cells in vitro was evaluated along with the in vivo therapeutic potential of combining radiation treatment with Pluronic in nude mice bearing Gli36 xenografts.

Materials and Methods

Formulation of Pluronic Solutions

Pluronics L10, L61, and L64 (molecular weight (Mw) of 3200, 2000, and 2900 Da, and average PPO/PEO units of 49.7/7.3, 31/4.55, and 30/26.4) were used. Pluronic L61 was generously donated by BASF (Shreveport, La.) and Pluronic L10 and L64 were purchased from Sigma Aldrich (Milwaukee, Wis.). Pluronic stock solutions were prepared by dissolving each polymer in DMEM medium overnight at 4° C. at concentration of 25 mg/ml. Solutions were filtered with a sterile 0.22 μm syringe filter (Millipore, Mass.) and test solutions (0.1-0.3 mg/ml) were prepared by diluting stock solutions and stored at 4° C. until use.

Cell Culture

Human Gli36Δ5 cells were cultured in complete DMEM medium (10% fetal bovine serum, 1% penicillin/streptomycin; Invitrogen, CA). Cells were cultured at 37° C. and 5% $CO_2$ in a humidified atmosphere. Cells were passaged at 90% confluence. Twenty four hours before treatment, cells were detached with 0.25% trypsin-EDTA and plated onto 96 well plates or 6 well plates ($1 \times 10^5$ cell/ml) as required for each assay.

Drug Sensitivity Assay

Cell viability was measured using mitochondrial succinate dehydrogenase assay (WST-1 assay; Biosciences, San Francisco, Calif.). After 24 hrs incubation of cells in 96 well plates, medium was aspirated and cells were incubated with 100 μl of Pluronic (L61, L64, and L10) test solutions (0.1 to 0.3 mg/ml) for 1 hr at 37° C. After the pretreatment, cells were replenished with fresh medium and recovered at 37° C. humidified incubator for 24 hrs. The assay was performed following manufacturer directions. Briefly, medium was removed and 100 μl of diluted reagent (1:9 with incomplete medium) was added and incubated at 37° C. for 1 hr. The optical density at 450 nm was determined using a plate reader (TECAN; Durham, N.C.). All studies were repeated in triplicate.

Protein Biomarker Analysis

For immunoblot analysis whole cell lysates were prepared according to standard protocols. In brief, cells were cultured in Petri dishes and irradiated using γ-radiation (rate of 3.2 Gy/min) at the dose of 3 Gy with or without 0.3 mg/ml Pluronic L10 treatment (1 hr). At different time points (5, 24 hours of post treatment), cells were lysed on ice for 15-30 min in a lysis buffer (Cell Signaling Technology, Beverly, Mass.) and centrifuged at 10,000 g for 10 min at 4° C. A Bio-Rad (Hercules, Calif.) protein assay kit was used to determine protein concentration in the supernatant. Protein was electrophoresed on sodium dodecyl sulfate/polyacrylamide gels and transferred to nitrocellulose membranes. Membranes were blocked with 5% nonfat dry milk in TBST buffer (0.1% Tween-20, 20 mM of Tris-HCl; pH 7.5, and 140 mM of NaCl). Membranes were then incubated with primary antibodies against Hsp90, Hsp70, and β-actin (Assay Designs/Stressgen, Ann Arbor, Mich.), followed by secondary antibody/horseradish peroxidase conjugates (Pierce, Ill.). The SNAP id system (Millipore, Mass.) was used for the antibody incubation. Horseradish peroxidase (HRP) substrate-luminal reagent (Millipore, Mass.) was used to detect chemiluminescence signal and photographed by Alpha Imager HP (Cell Biosciences, CA). For in vivo Hsp analysis, tumor xenografts were excised from each group of nude mice and tissue samples were prepared by homogenizing the piece of dissected tumor in lysis buffer, followed by centrifugation at 4° C. and collecting the supernatant. The Western blot analysis was carried out as described above.

Clonogenic Survival Assay

Cell survival was measured by the colony formation ability of treated cells using the clonogenic assay. Cells were plated in 6 well plates and after 24 hrs, irradiated with γ-rays (0-8 Gy) using a cesium-137 chamber with or without 1 hr pretreatment of Pluronic L10 (0.1 and 0.3 mg/ml). Untreated and treated cells were trypsinized, counted, diluted and seeded in 6 well plates in duplicates and cultured for 10 days. Colonies were fixed with methanol (Fisher, Pittsburgh, Pa.) stain with May-Grunwald stain (EMD chemicals, Gibbstown, N.J.) and Giemsa solution (Sigma Aldrich, St. Louis, Mo.). Colonies containing more than 50 cells were counted using a cell counter. The assay was triplicated and calculated the survival fraction. The dose enhancement factor (DEF) for Pluronic L10 treatment was calculated as the ratio of dose of radiation to 50% reduction of colony/dose of radiation+Pluronic to 50% reduction of colony.

Neutral Comet Assay

Single cell electrophoresis assay or comet assay was performed for evaluating the formation of double strand breaks following the cell exposure to 0.3 mg/ml Pluronic L10 alone, radiation alone (3 Gy), and combined treatment. After different time points (t=0, 3, 6, 24 hrs), treated cells were collected, embedded in agarose gel on a slide (Trevigen, Gaithersburg, Md.) and subjected to lysis followed by electrophoresis under neutral conditions. During the electrophoresis damaged DNA travels away from the nucleus while intact DNA remains without migrating. The slides were stained with the SYBER green and examined under the fluorescence microscope. The amount of DNA damage was measured by analyzing the tail moment of migrated DNA using the Comet score image analysis software. Comet tail moment is calculated as the product of tail length and the fraction of DNA in the tail for each treatment and each time points. All comets were quantified by two independent observations (scored 75 cells in each).

Measurement of γ-H2AX

More quantitative results of DNA damage were obtained using flow cytometry analysis of γ-H2AX. Cells were irradiated (3 Gy) with and without 1 hr pretreatment of 0.3 mg/ml Pluronic L10. At different time points (t=0, 1, 2, 4, 24 hrs) of post treatment cells were trypsinized, collected (~$10^6$ cells), and fixed with methanol. Cell samples were rinsed with PBS, centrifuged and resuspended in 200 μl of mouse monoclonal anti-phospho-histone H2AX antibody with 1:500 dilution (Millipore, Mass.) at 4° C. for 1 hr. Cells were washed with PBS/BSA and then resuspended in 4,6-diamidino-2-phenylindole (DAPI; Sigma Aldrich, St. Louis, Mo.). DNA double-strand breaks were determined by the presence of γH2AX staining as detected by flow cytometry analysis. The measurements were conducted by BD LSR II flow cytometer (BD Biosciences, San Jose, Calif.) and cells were excited with the 488 nm lasers. The data analysis was performing using WinList 3D 6.0 (Verity Software House, Topsham, Me.).

Animal Studies

In all procedures, the animals were anesthetized with inhalation of ketamine/xylazine cocktail with 1 L/min oxygen. Gli36 ($3 \times 10^5$) cells were suspended in growth medium and matrigel (BD biosciences, San Jose, Calif.) in 1:2 ratio and injected subcutaneously into the flank of athymic nude mice (28 total mice). After 10 days of inoculation, mice were equally divided into 7 groups. Three groups (control group and radiation only groups) received 100 μl of saline and the other 4 groups (Pluronic only and Pluronic+radiation groups) received 100 μl of 0.3 mg/ml Pluronic L10 by intravenous injection (IV). One hr after Pluronic L10 or saline administration, flank tumors in radiation only and Pluronic+radiation groups were irradiated in a Cs-137 chamber (3 Gy) covering the rest of the body customized lead jig for shielding. After 5 and 24 hrs of post treatment, animals were euthanized with carbon dioxide inhalation and tumors were excised and stored at −80° C. for protein analysis and histology studies.

Apoptosis Analysis by TUNEL Assay

The apoptosis of irradiated tumor xenografts was analyzed using the Terminal deoxynucleotidyl transferase dUTP nick end labeling (TUNEL) assay (Promega, Madison, Wis.). Tumor xenografts bearing mice were irradiated as explained above and tumors were excised at 5 hrs and 24 hrs after treatment. Tumor tissue sections were fixed in 4% paraformaldehyde for 15 min, washed and labeled with solution containing terminal deoxynucleotidyl transferase (TdT) reaction buffer, TdT enzyme, and biotinylated nucleotide for 1 hr at 37° C. in humidified atmosphere. The tissue sections were washed and DAPI was added for positive staining of cells. The TUNEL staining was observed under the fluorescence microscope and analyzed for the positive staining using Axio-Vision V 4.8 software (Thornwood, N.Y.). The sites that show the TUNEL indicate apoptosis of the tumor, allowing for quantitative data analysis.

Results

Pluronics are Relatively Non-Toxic to Gli36 Cells

Figure 12:
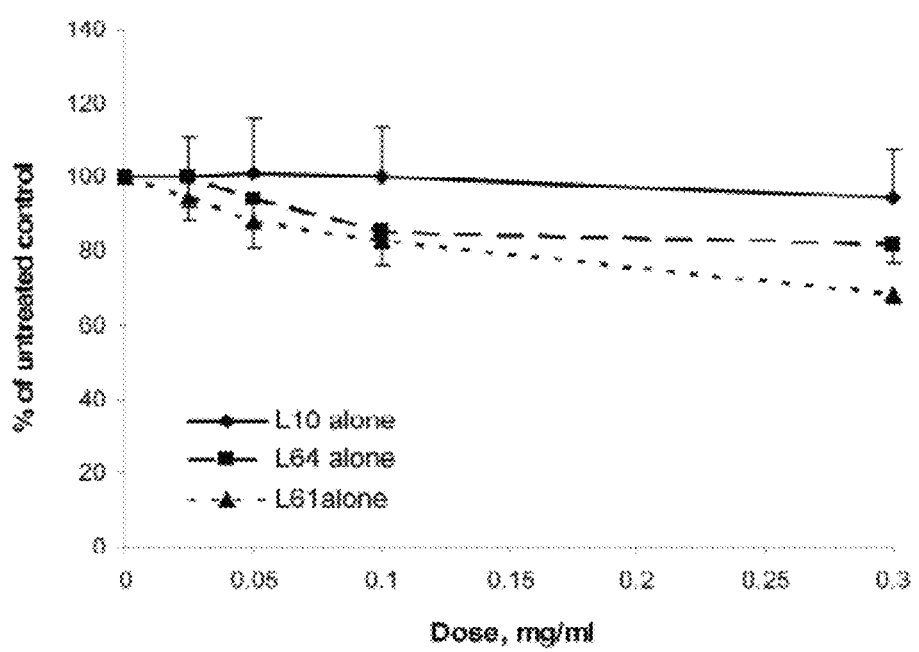
FIG. 12 illustrates a plot showing cell viability of Gli36 cells after exposure to serial dilution of Pluronic L10, L64, and L61 for 1 hr. The cell viability was tested 24 hrs after treatment using the WST-1 assay.

FIG. 12 shows the relative cell viabilities after 1 hr pre-exposure to Pluronics L10, L64, and L61. Cells were treated with Pluronics (L10, L64, and L61) ranging in concentration from 0-0.3 mg/ml. Cell viability was analyzed 24 hrs after treatment using the WST-1 assay. Results demonstrated loss of cell viability is not prominent at low doses (~0.025 mg/ml) of Pluronic L10, L64, and L61. However, cells were more sensitive for high doses (0.1-0.3 mg/ml) of Pluronic L64 and L61. Viability of cells treated with 0.3 mg/ml of Pluronic L64 was 81±5% of untreated control. The most cytotoxicity was observed in cells treated with Pluronic L61, which reduced the percent of cell viability to 70±3% of untreated control. As seen in FIG. 12 (A), Pluronic L10 treatment maintained enzyme activity higher than 94±13% for all tested concentration ranges. The results demonstrate the relative non-cytotoxicity of Pluronic L10 with Gli36 cells. On the basis of cytotoxicity data, Pluronic L10 with 0.3 mg/ml dose was selected as the sensitizer for subsequent radiation experiments.

Pluronic L10 Sensitizes Gli36 Cells to Radiation

Figure 13:
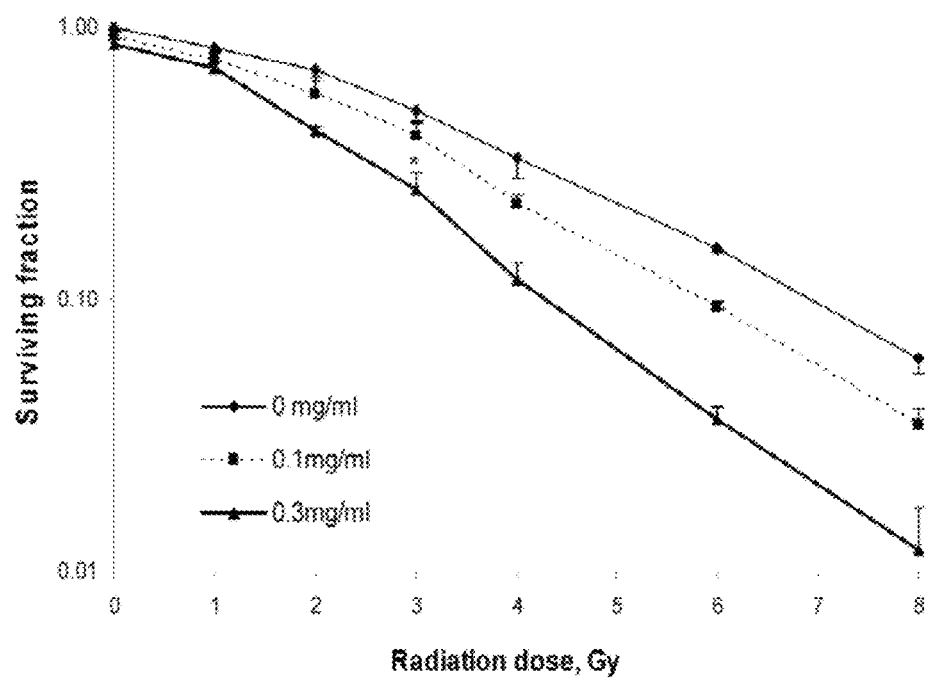
FIG. 13 illustrates a plot showing clonogenic survival in Gli36 cells after irradiation with radiation doses from 0-8 Gy, with and without 1 hr pretreatment with Pluronic L10 (0.1 and 0.3 mg/ml).

To test the effects of Pluronic L10 on radiosensitivity of Gli36 cells, clonogenic assays were performed after 0-8 Gy of irradiation with and without 1 hr pretreatment of 0.1 and 0.3 mg/ml Pluronic L10. The cell survival curves after each treatment are presented in the FIG. 13. A significant radiosensitization effect of Pluronic L10 was achieved with the Pluronic L10 concentration of 0.3 mg/ml compared to the radiation only treatment (P<0.01) with observed $DEF_{0.5}$ of 1.34. Higher DEF value indicates the performance of Pluronic as a radiosensitizer.

Effect of Pluronic L10 on Hsp90 Level

Figure 14:
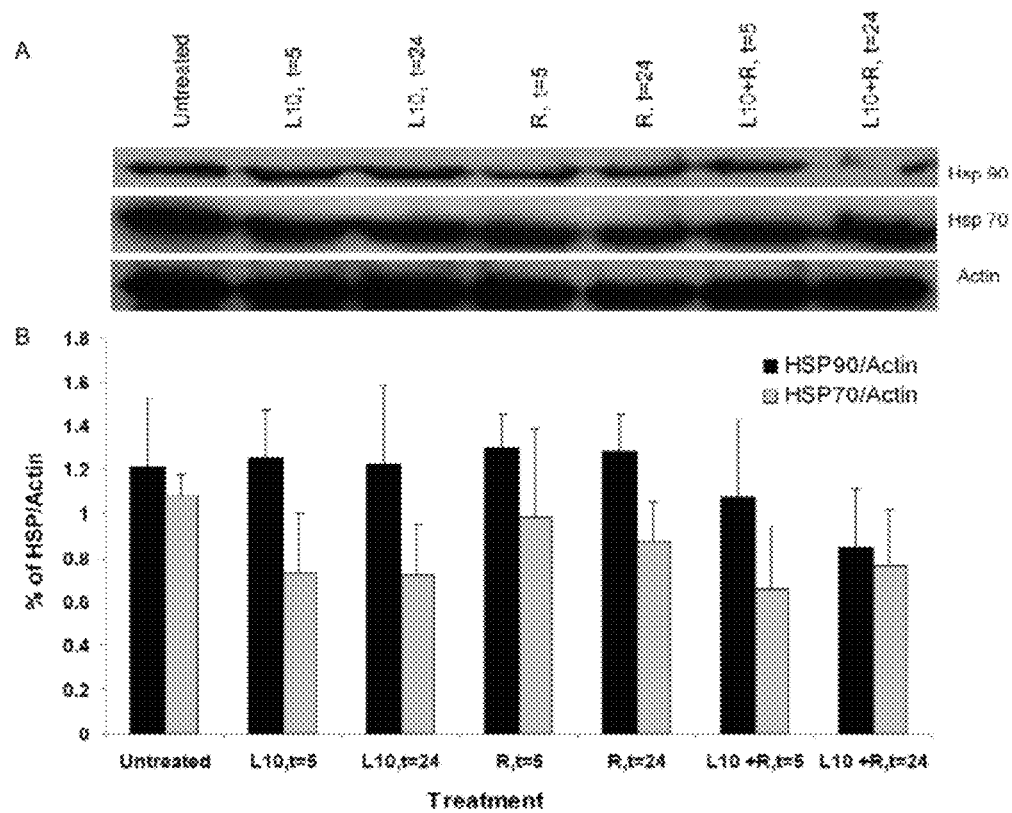
FIG. 14 illustrates: (A) a Western blot of in vitro Hsp90 and Hsp70 level after 1 hr pretreatment of Pluronic L10 (0.3 mg/ml), radiation only (3 Gy), and combined treatment; and (B) a table showing Hsp expression at different time points normalized versus actin.

Hsp90 and Hsp70 expression in Gli36 cells after irradiation (3 Gy) was determined by immunoblot analysis. Cells were irradiated with and without 1 hr pretreatment of Pluronic L10 and cells were returned to the 37° C. incubator. At different time points (t=5 hrs and t=24 hrs), cell lysates were collected and analyzed for Hsp90 and Hsp70. FIG. 14 shows Hsp90 and Hsp70 protein levels at different post treatment time points (n=3). Twenty four hrs after combined treatment, the Hsp90 level was reduced by 30.44% compared to the untreated control. Interestingly, in the same manner, Hsp70 level also decreased by 28.86% at 24 hrs post-treatment of combined treatment compared to the untreated control.

Pluronic L10 Increases the DNA Double Strand Break

Figure 15:
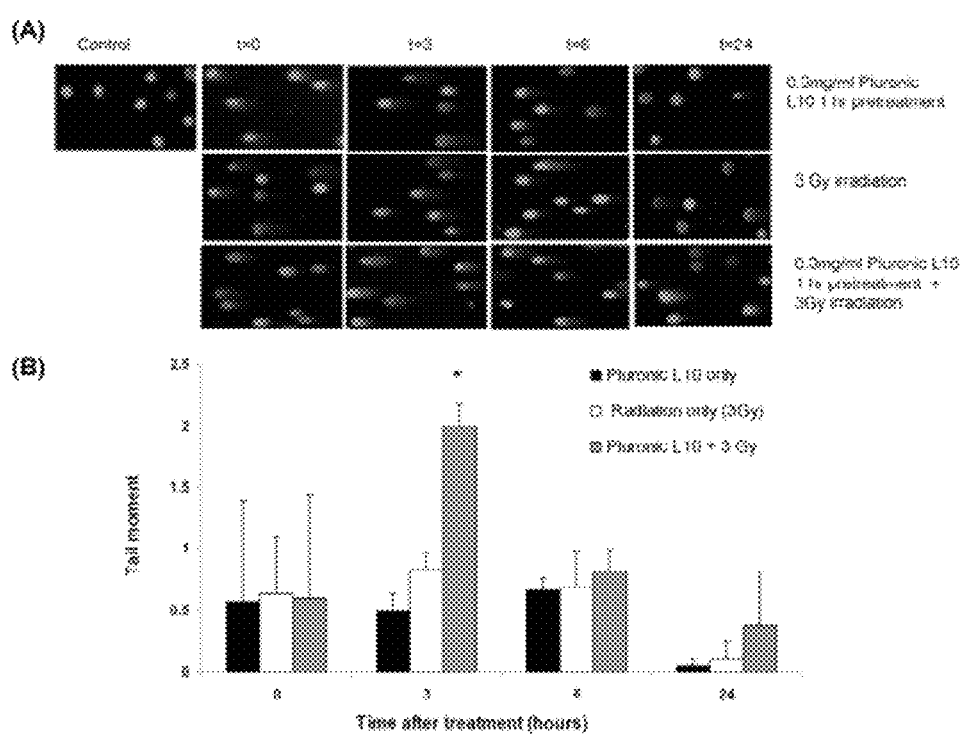
FIG. 15 illustrates: (A) comet images of Gli36 cells obtained from neutral single-cell gel electrophoresis (SCGE) after treatment with 0.3 mg/ml L10 (1 hour), 3 Gy radiation, and combination of L10 and radiation: and (B) a table showing comet tail moment for each treatment and each time point.

As shown in FIG. 15, cells containing damaged DNA were observed as comet with a bright head and elongated tail. In contrast, healthy DNA emerged as an intact nucleus with no tail. Seventy five randomly selected, individual, and non-overlapping cells were scored for DNA damage analysis. As expected, DNA damage was observed after treatment with radiation alone and Pluronic L10+radiation. Three hours after treatment, all samples showed maximum DNA damage. The tail moment of the radiation only treated cells was 0.83±0.14, but when radiation was combined with Pluronic L10, the tail moment was 1.99±0.18 (P<0.01). Interestingly, 24 hrs after combined treatment, the DNA damage was higher compared to individual treatments at the same time point.

Pluronic L10 Increases the γ-H2AX Foci Formation in Gli36 Cells

To further elucidate the effect of Pluronic L10 on DNA damage repair, flow cytometry was performed by analyzing the phosphorylated histone $H_2AX$ ($\gamma$-$H_2AX$). Cells were exposed to Pluronic L10 for 1 hr, irradiated with 3 Gy and at different time points, cell samples were fixed, stained and analyzed for $\gamma$-$H_2AX$ staining. As demonstrated in FIG. 17, immediately after combined treatment, $\gamma$-$H_2AX$ staining was increased compared to the untreated and control groups. The $\gamma$-$H_2AX$ foci were elevated 2 hrs after combined treatment compared to the radiation only control (P<0.1). After the 2 hr time point, phosphorylation of $\gamma$-$H_2AX$ decreased over time and lower staining was observed. Similar to comet assay results, the reduction of $\gamma$-$H_2AX$ staining is modest 24 hrs after combined treatment compared to the individual treatments (P<0.5). These results reflect the low extent of DNA DSB repair mechanism occurs as an effect of Pluronic L10 radiosensitivity.

Pluronic L10 Decreases the Level of Hsp90 in Tumor Xenografts

To investigate the in vivo potential of combining Pluronic L10 and irradiation, Gli36 cells were inoculated in nude mice. The tumor xenografts were irradiated with and without Pluronic L10 and tissue lysates were collected as described in methods sections. FIG. 17 shows the representative immunoblot of in vivo Hsp analysis. Hsp90 levels within tumor tissues decreased by 67.9% at 24 hrs with combined treatment compared to the untreated control tumors. In addition, 24 hrs after the combined treatment, Hsp70 levels in tumor tissues decreased by 26.63% compared to untreated control. The data indicates the potential of using Pluronic L10 in reducing both Hsp90 and Hsp70 in vivo to increase the efficacy of radiotherapy.

Pluronic L10 Sensitizes Tumors to Radiotherapy in Nude Mice by Increasing Apoptosis Histological examination of Gli36 tumor xenografts using the TUNEL assay (FIG. 18) demonstrated differences in apoptosis between each treatment condition. Results illustrate that radiation induced apoptosis at both time points (5 hrs and 24 hrs of post treatment) is higher in combined treatment (43.34±1.99% at t=5 hrs and 42.53±4.26% at t=24 hrs) compared to individual treatments (Pluronic L10 only: 17.80±2.19% at t=5 hrs and 14.76±1.01% at t=24 hrs, Radiation only: 29.2±1.05% at t=5 hrs and 25.59±0.38% at t=24 hrs) with p<0.01. Importantly, amount of apoptosis decreased to a greater extent one day after individual treatments (17.04%, 12.36% decreased for Pluronic L10 and radiation only respectively) compared to the combined treatment (1.8%). These data demonstrate the additive effect of Pluronic L10 in elevation of apoptosis and consequently sensitizing radiotherapy in Gli36 tumor xenograft model.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, the following is claimed:

1. A method of treating a tumor or cancer in a subject, the method consisting essentially of:
   administering to cancer or tumor cells of the subject a radiation sensitizing amount of a poly(ethylene oxide)- poly(propylene oxide) copolymer, the copolymer having a molecular weight of about 1100 Da to about 3200 Da and a hydrophilic lipophilic balance (HLB) of about 1 to about 8; and administering radiation therapy to the cancer or tumor cells sensitized by the poly(ethylene oxide)-poly(propylene oxide) copolymer.

2. The method of claim 1, the tumor or cancer being radiation resistant and the administered poly(ethylene oxide)-poly(propylene oxide) copolymer sensitizing the tumor or cancer cells to radiation therapy.

3. The method of claim 1, the poly(ethylene oxide)-poly(propylene oxide) copolymer being administered at an amount effective to reduce Hsp expression and/or function in the cancer cell or tumor cell induced by radiation therapy.

4. The method of claim 1, the copolymer being selected from the group consisting of poloxamers, poloxamines, and combinations thereof.

5. The method of claim 4, the poloxamer comprising the chemical formula of:

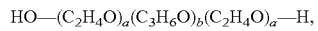

where "a" is about 2 to about 130 and "b" is about 16 to about 67.

6. The method of claim 1, the poly(ethylene oxide)-poly(propylene oxide) copolymer being administered directly to the tumor or cancer cells.

7. The method of claim 1, the poly(ethylene oxide)-poly(propylene oxide) copolymer being administered systemically to the subject.

8. The method of claim 7, the poly(ethylene oxide)-poly(propylene oxide) copolymer being administered parenterally or by intravenous injection.

9. The method of claim 1, wherein the poly(ethylene oxide)-poly(propylene oxide) copolymer has a dose enhancement factor (DEF) of at least 1.3.

10. A method of treating a tumor or cancer in a subject, the method consisting essentially of:

administering to cancer or tumor cells of the subject a radiation sensitizing amount of a poloxamer comprising the chemical formula $HO-(C_2H_4O)_a(C_3H_6O)_b(C_2H_4O)_a-H$ where "a" is about 2 to about 130 and "b" is about 16 to about 67, the poloxamer having a molecular weight of about 1100 Da to about 3200 Da and a hydrophilic lipophilic balance (HLB) of about 1 to about 8; and applying ionizing radiation to the cancer or tumor cells sensitized by the poloxamer.

11. The method of claim 10, the tumor or cancer being radiation resistant and the administered poloxamer sensitizing the tumor or cancer cells to ionizing radiation.

12. The method of claim 10, the poloxamer being administered at an amount effective to reduce Hsp expression and/or function in the cancer cell or tumor cell induced by ionizing radiation.

13. The method of claim 10, the poloxamer being administered directly to the tumor or cancer cells.

14. The method of claim 10, the poloxamer being administered systemically to the subject.

15. The method of claim 14, the poloxamer being administered parenterally or by intravenous injection.

16. The method of claim 10, wherein the poloxamer has a dose enhancement factor (DEF) of at least 1.3.

17. A method of treating a radiation resistant tumor or cancer in a subject, the method consisting essentially of:

administering to radiation resistant cancer or tumor cells of the subject a radiation sensitizing amount of a poloxamer comprising the chemical formula $HO-(C_2H_4O)_a(C_3H_6O)_b(C_2H_4O)_a-H$, where "a" is about 2 to about 130 and "b" is about 16 to about 67 and having a molecular weight of about 1100 Da to about 3200 Da and a hydrophilic lipophilic balance (HLB) of about 1 to about 8; and applying ionizing radiation to the cancer or tumor cells sensitized by the poloxamer.

18. The method of claim 17, the cancer being selected from the group consisting of gliomas, glioblastoma multiform (GBM), colorectal cancer, breast cancer, liver cancer, and melanoma.

19. The method of claim 17, wherein the poloxamer has a dose enhancement factor (DEF) of at least 1.3.

20. The method of claim 1, the cancer being selected from the group consisting of gliomas and colorectal cancer.

21. The method of claim 10, the cancer being selected from the group consisting of gliomas and colorectal cancer.

22. The method of claim 17, the cancer being selected from the group consisting of gliomas and colorectal cancer.

* * * * *